(12) United States Patent
Herron et al.

(10) Patent No.: US 9,332,842 B2
(45) Date of Patent: May 10, 2016

(54) SLIDING HINGES AND RELATED METHODS AND DEVICES SUITABLE FOR APPARATUS FOR AUTOMATED EVALUATION OF MICROORGANISM GROWTH IN TEST SAMPLES

(71) Applicant: bioMerieux, Inc., Durham, NC (US)

(72) Inventors: Michael A. Herron, Overland Park, KS (US); Lawrence Guerra, Mission, KS (US); Kent C. Smith, St. Charles, MO (US); Mark Joseph Fanning, Florissant, MO (US)

(73) Assignee: bioMérieux, Inc., Durham, NC (US)

( * ) Notice: Subject to any disclaimer, the term of this patent is extended or adjusted under 35 U.S.C. 154(b) by 390 days.

(21) Appl. No.: 13/800,056

(22) Filed: Mar. 13, 2013

(65) Prior Publication Data

US 2013/0257238 A1    Oct. 3, 2013

Related U.S. Application Data

(60) Provisional application No. 61/616,586, filed on Mar. 28, 2012.

(51) Int. Cl.
| | | |
|---|---|---|
| *A47B 96/00* | (2006.01) | |
| *A47B 81/00* | (2006.01) | |
| *C12M 1/00* | (2006.01) | |

(Continued)

(52) U.S. Cl.
CPC ............... *A47B 96/00* (2013.01); *A47B 81/00* (2013.01); *C12M 41/14* (2013.01); *C12M 41/36* (2013.01); *E05D 3/022* (2013.01); *E05D 3/06* (2013.01); *E05Y 2400/654* (2013.01);

(Continued)

(58) Field of Classification Search
CPC ....... A47B 81/00; A47B 96/00; C12M 41/14; C12M 41/36; E05D 3/022; E05D 3/06; E05Y 2400/654; E05Y 2800/344; E05Y 2900/20; E05Y 2900/608
USPC ................. 312/209, 265, 325, 295, 310, 311; 435/287.3, 303.1
See application file for complete search history.

(56) References Cited

U.S. PATENT DOCUMENTS 4,154,320 A * 5/1979 Jatczak ................... A62B 1/20
                                                        182/48
4,932,160 A    6/1990 Sperko
(Continued)

FOREIGN PATENT DOCUMENTS

DE    102005057586    5/2007
GB         2209051    4/1989

OTHER PUBLICATIONS

International Preliminary Report on Patentability for PCT application No. PCT/US2013/033708, date of issuance Oct. 1, 2014, 10 pages.

(Continued)

*Primary Examiner* — Nathan Bowers
*Assistant Examiner* — Lydia Edwards
(74) *Attorney, Agent, or Firm* — Myers Bigel & Sibley, P.A.

(57) ABSTRACT

Devices and systems include housing members with sliding hinges that allow straight linear outward extension before allowing the front housing member to pivot open provide access to interiors for service using smaller footprints and/or without disrupting abutting instrument operation.

22 Claims, 19 Drawing Sheets

(51) Int. Cl.
*E05D 3/02* (2006.01)
*E05D 3/06* (2006.01)
*C12M 1/34* (2006.01)

(52) U.S. Cl.
CPC ....... *E05Y 2800/344* (2013.01); *E05Y 2900/20* (2013.01); *E05Y 2900/608* (2013.01)

(56) References Cited

U.S. PATENT DOCUMENTS

| | | |
|---|---|---|
| 4,945,060 A | 7/1990 | Turner et al. |
| 5,094,955 A | 3/1992 | Calandra et al. |
| 5,162,229 A | 11/1992 | Thorpe et al. |
| 5,164,796 A | 11/1992 | Guiseppi et al. |
| 5,217,876 A | 6/1993 | Turner et al. |
| 5,443,312 A * | 8/1995 | Schluter ............... H05K 7/1488 312/201 |
| 5,795,773 A | 8/1998 | Read et al. |
| 5,856,175 A | 1/1999 | Thorpe et al. |
| 7,901,019 B2 * | 3/2011 | Laundroche ............ D06F 37/28 312/325 |
| 8,100,488 B2 * | 1/2012 | Eisele ................... F25D 23/067 108/106 |
| 2002/0140327 A1 * | 10/2002 | Kim ........................ E05B 65/46 312/311 |
| 2004/0160147 A1 * | 8/2004 | Bochner ............ A61B 19/0248 312/209 |
| 2005/0006994 A1 * | 1/2005 | Rapier, III .............. A47B 77/18 312/311 |
| 2007/0018545 A1 * | 1/2007 | Calabria ................ A47B 77/10 312/311 |
| 2008/0265727 A1 | 10/2008 | Kohlman et al. |
| 2010/0068755 A1 | 3/2010 | Walsh et al. |
| 2011/0124028 A1 | 5/2011 | Robinson et al. |
| 2013/0265844 A1 | 10/2013 | Yuan et al. |

OTHER PUBLICATIONS

International Search Report for PCT application No. PCT/US2013/033708, date of mailing Jan. 7, 2013, 5 pages.

* cited by examiner

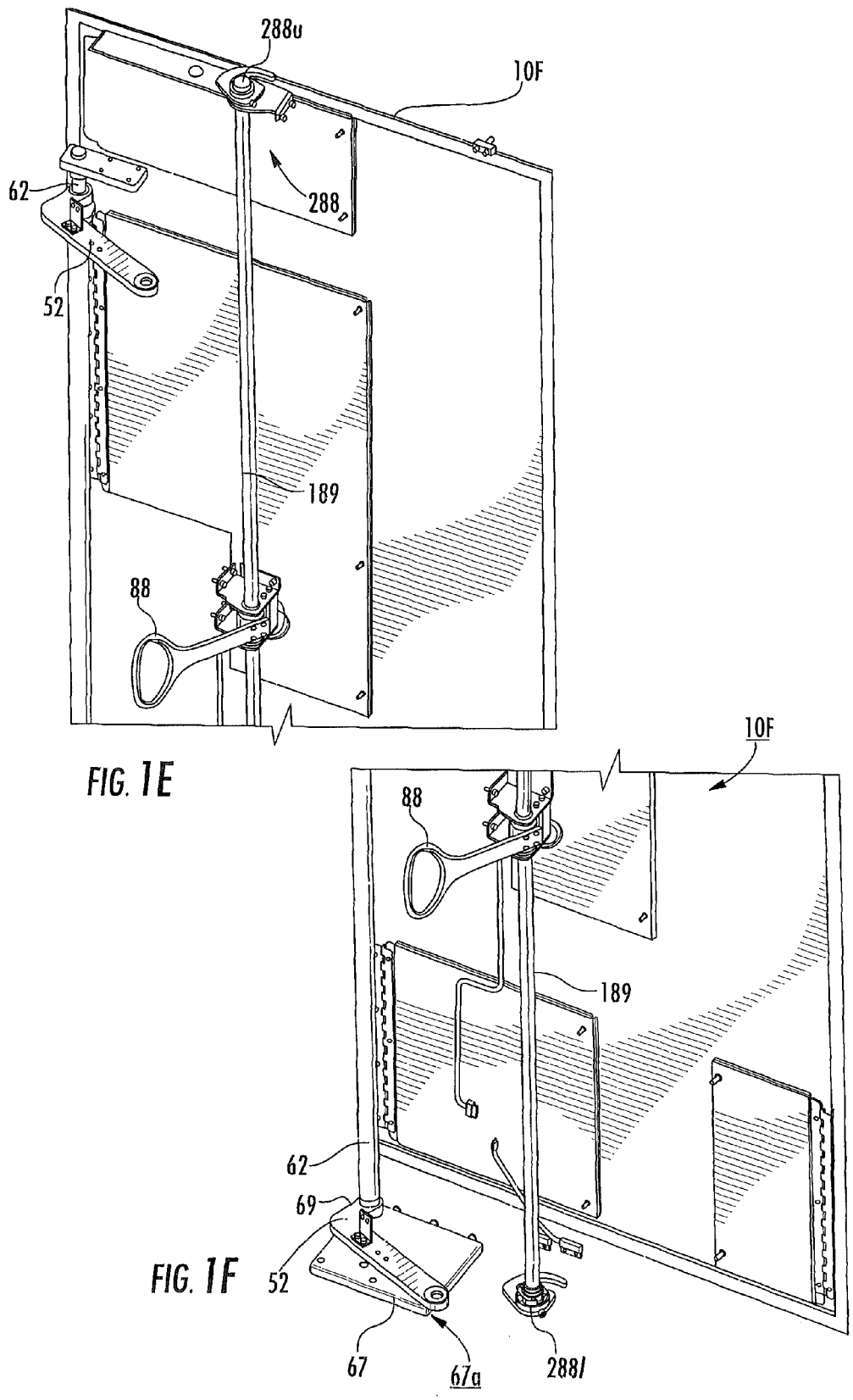

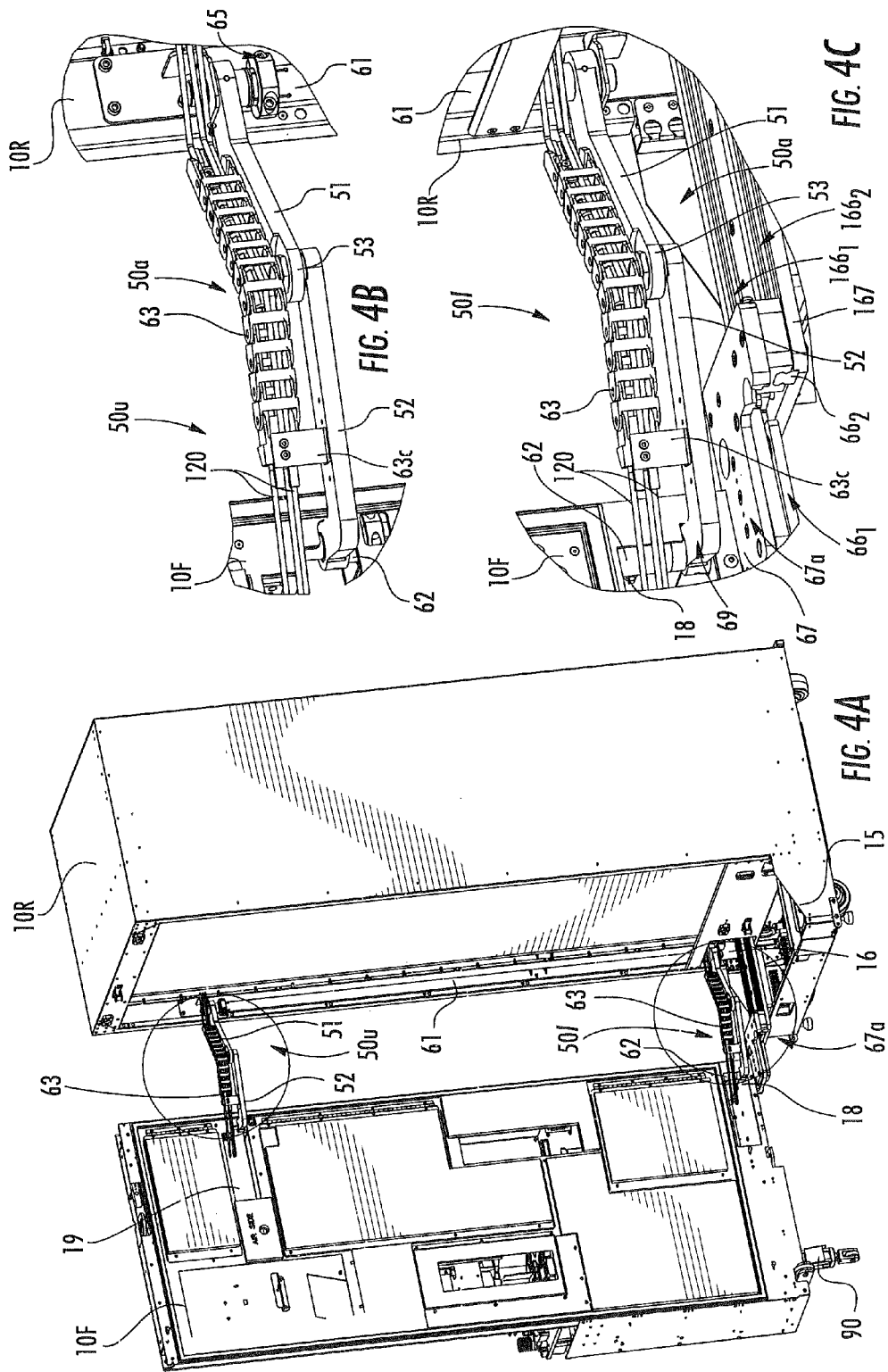

SLIDING HINGES AND RELATED METHODS AND DEVICES SUITABLE FOR APPARATUS FOR AUTOMATED EVALUATION OF MICROORGANISM GROWTH IN TEST SAMPLES

RELATED APPLICATIONS

This application claims the benefit of and priority to U.S. Provisional Application Ser. No. 61/616,586, filed Mar. 28, 2012, the contents of which are hereby incorporated by reference as if recited in full herein.

BACKGROUND

Automated Microbial Detection Apparatus, such as described in U.S. 2011/0124028, describe housings with an enclosed climate controlled chamber. The apparatus holds a power supply and various operational components that may need servicing over time. The content of this application is hereby incorporated by reference as if recited in full herein.

SUMMARY

Embodiments of the invention are directed to sliding hinges for housings with cantilevered doors or structures that can allow access to an interior of the housing.

Some embodiments are directed to housings that include: (a) a front housing member; (b) a rear housing member; (c) an upper hinge assembly with first and second linkages, the first and second linkages each having opposing first and second end portions, wherein the first linkage second end portion is pivotably attached to the second end portion of the second linkage, the first linkage first end portion is attached to the front housing member, and the second linkage first end portion is attached to the rear housing member; and (d) a lower hinge assembly with first and second linkages and a linear slide assembly, the first and second linkages each having opposing first and second end portions, wherein the first linkage second end portion is pivotably attached to the second end portion of the second linkage, the first linkage first end portion is attached to the front housing member, and the second linkage first end portion is attached to the rear housing member. The linear slide assembly resides in a lower portion of the rear housing member under the first or second linkages of the lower hinge assembly and slidably engages the front housing member to define a straight linear movement of the front housing member out from the rear housing member.

The linear movement may be for a defined distance "D" that is between about 2-12 inches.

The first end portion of the first linkage of the lower hinge assembly can have an outer portion that is slidably attached to the front housing member so as to be able to travel in a space in the front housing member to control a pivot angle of the front housing member. The front housing member can be configured to pivot open to an angle of between about 60-120 degrees only after the front housing member is in an extended position associated with the straight linear movement.

The housing can include first and second vertical rods that extend between the upper and lower hinge assemblies. The first vertical rod can reside in the front housing member with an upper end portion of the first vertical rod attached to the first end portion of the first linkage of the upper hinge assembly and a lower end portion is attached to the linear slide assembly. The second vertical rod can reside in the rear housing member with an upper end portion of the second vertical rod attached to the first end portion of the second linkage of the upper hinge assembly. The lower end portion of the second vertical rod can be attached to the first end portion of the second linkage of the lower hinge assembly. The first and second linkages of the upper and lower hinge mechanisms can extend outwardly in concert as the front housing member travels straight outwardly to open the housing.

The first and second linkages of at least one of the upper and lower hinge assemblies can include cable carrier attachment members for holding cable carriers that route power and/or data cables between components in the front and rear housing members.

The upper hinge assembly can be adjustably attached to the front housing member and/or the rear housing member so as to be able to provide for longitudinal adjustment for alignment of the front and rear housing members.

The linear slide assembly can include upper and lower cooperating plates that define at least one slide rail therebetween. The upper plate can be configured to slide in and out while attached to the lower plate, with the lower plate affixed to a base of the rear housing member.

The linear slide assembly comprises first and second horizontally-oriented rigid, planar substrates with first and second parallel rails that cooperate with a corresponding slot to define linear slide tracks for the linear slide assembly.

The front housing member can weigh at least about 50 pounds. The housing can enclose a climate controlled chamber. The rear housing member has an interior volume that is larger than that of the front housing member. The rear housing member can have a plurality of wheels that reside on a floor and has a raised front base portion that resides under the lower hinge assembly.

The front housing member has a stowable kick stand that can be deployed into position when the front housing member is opened.

The front housing member can include a kick stand assembly with a rear wheel that contacts a surface of a base in the rear housing member when the housing is in a closed or partially open configuration. The kick stand can extend vertically down when the rear wheel is forward of the base surface and when the front housing member is spaced apart a distance from the rear housing member.

Other embodiments are directed to automated detection apparatus for detection of microorganism growth in test samples. The apparatus includes: (a) a housing enclosing an interior temperature controlled chamber, the housing having a front housing member and a rear housing member; (b) a detection device located within the housing configured to detect microorganism growth in specimen containers loaded into the housing; (c) an upper hinge assembly with first and second linkages, the first and second linkages each having opposing first and second end portions, the first linkage second end portion is pivotably attached to the second end portion of the second linkage, the first linkage first end portion is attached to the front housing member, and the second linkage first end portion is attached to the rear housing member; (d) a lower hinge assembly with first and second linkages, the first and second linkages each having opposing first and second end portions, wherein the first linkage second end portion is pivotably attached to the second end portion of the second linkage, the first linkage first end portion is attached to the front housing member, and the second linkage first end portion is attached to the rear housing member; and (e) a linear slide assembly attached to the front and rear housing members and residing under the first or second linkages of the lower hinge assembly that slidably engages the front housing member to define a straight linear movement of the front housing member out from the rear housing member.

The linear movement can be for a defined distance "D" that is between about 2-12 inches.

The first end portion of the lower hinge assembly first linkage can have an outer portion that is slidably attached to the front housing member so as to be able to travel in a space in the front housing member to control a pivot angle of the front housing member. The front housing member can pivot open to an angle of between about 60-120 degrees only after the front housing member is in an extended position associated with the straight linear movement.

The apparatus can include first and second vertical rods that extend between the upper and lower hinge assemblies. The first vertical rod can reside in the front housing member with an upper end portion of the first vertical rod attached to the first end portion of the first linkage of the upper hinge assembly and a lower end portion is attached to the linear slide assembly. The second vertical rod can reside in the rear housing member with an upper end portion of the second vertical rod attached to the first end portion of the second linkage of the upper hinge assembly. The lower end portion of the second vertical rod can be attached to the first end portion of the second linkage of the lower hinge assembly. The first and second linkages of the upper and lower hinge mechanisms can extend outwardly in concert as the front housing member travels straight outwardly to open the housing.

The first and second linkages of at least one of the upper and lower hinge assemblies can include cable carrier attachment members for holding cable carriers that route power and/or data cables between components in the front and rear housing members.

The upper hinge assembly can be adjustably attached to the front housing member and/or the rear housing member so as to be able to provide for longitudinal adjustment for alignment.

The linear slide assembly can include upper and lower cooperating plates that define at least one slide rail therebetween, the upper plate configured to slide in and out while attached to the lower plate, with the lower plate affixed to a base of the rear housing member.

The front housing member can have a kick stand assembly with a rear wheel that contacts a surface of a base in the rear housing member when the housing is in a closed or partially open configuration. The kick stand can automatically extend vertically down when the rear wheel is forward of the base surface (when the front housing member is spaced apart a distance from the rear housing member).

The apparatus can include a second housing adjacent the first housing, the distance "D" can be about 8 inches and the angle can be about 80 degrees.

Yet other aspects of the invention are directed to methods of opening a housing to allow access to an interior thereof. The methods include: (a) providing a housing having a rear housing member and a front housing member that are pivotably attached together at one long side; (b) sliding the front housing member straight out from the rear housing member a distance "D" that is between about 2-12 inches; then (c) pivoting the front housing member open to an angle of between about 60-120 degrees.

The housing can have upper and lower two-bar linkages and a pair of vertically oriented rods, one attached to the rear housing member and one attached to the front housing member and each also attached to a different link in the two-bar linkage. The lower linkage can also be attached to slide rails mounted to a base of the rear member to guide linear extension. The sliding step can be carried out so that the lower two-bar linkage is forced to slide along the rails and the upper and lower two-bar linkages are extended in concert to move one long end of the front housing member forward the distance D before allowing the pivoting.

The method may include automatically deploying a kick stand to extend downward to define a support for the first housing member in response to the sliding or pivoting of the front housing member.

The housing can have a linear slide assembly that defines the slide rails and includes a pivot plate that supports a vertical rod in the front housing member. The lower linkage can have an outer link that has an outer portion that is slidably trapped in a space in a lower corner of the front housing member to control when the front housing can pivot outward. The method can include mechanically locking the front housing member to travel straight outwardly using the position of the outer member in the front housing space and/or an orientation of the pivot plate, then mechanically controlling (i) when the front housing can pivot outwardly and (ii) the pivotable angle of the front housing member based on the position of the outer portion of the outer link in the front housing member and/or the travel distance "D" of the pivot plate.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 1E is a greatly enlarged view of an upper interior portion of the front housing member shown in FIG. 1A with the handle pulled outwardly according to embodiments of the present invention.

FIG. 1F is a greatly enlarged view of a lower interior portion of the front housing member shown in FIG. 1A with the handle pulled outwardly according to embodiments of the present invention.

FIG. 4A is a side perspective view of a housing with front and rear housing members that can open using a sliding hinge assembly according to embodiments of the present invention.

FIG. 4B is an enlarged view of an upper hinge assembly shown in the top circled region of FIG. 4A according to embodiments of the present invention.

FIG. 4C is an enlarged view of a lower hinge assembly shown in the lower circled region of FIG. 4A according to embodiments of the present invention.

DETAILED DESCRIPTION OF EMBODIMENTS OF THE INVENTION

Figure 1A:
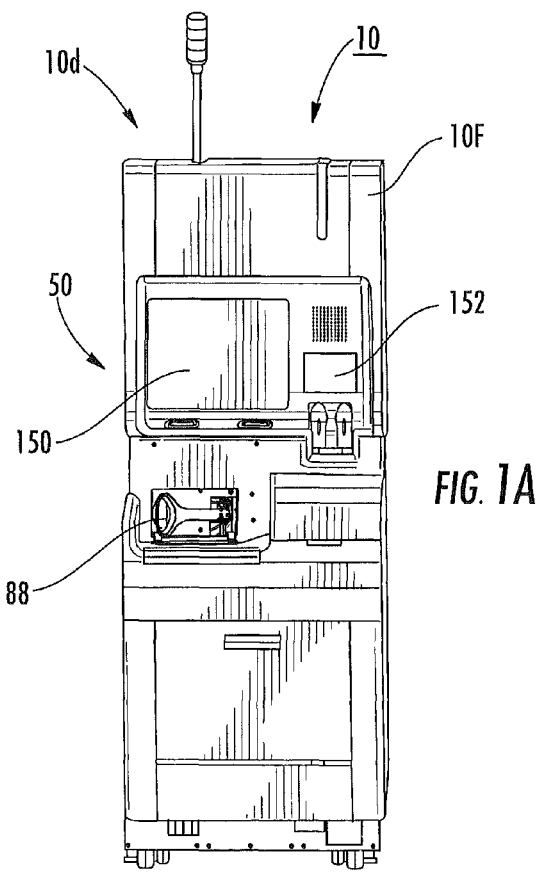
FIG. 1A is a front view of a housing with front and rear housing members that can open using a sliding hinge assembly according to embodiments of the present invention

The present invention will now be described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. Like numbers refer to like elements throughout. In the figures, the thickness of certain lines, layers, components, elements or features may be exaggerated for clarity. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. The phrase "in communication with" refers to direct and indirect communication. Although described or shown with respect to one embodiment, the features so described or shown can apply to other embodiments.

In the description of embodiments of the present invention that follows, certain terms are employed to refer to the positional relationship of certain structures relative to other structures. As used herein, the term "front" or "forward" and derivatives thereof refer to the general or primary direction that a container travels to enter a test or evaluation apparatus; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the directions opposite, respectively, the forward and downstream directions.

The term "circuit" refers to software embodiments or embodiments combining software and hardware aspects, features and/or components, including, for example, at least one processor and software associated therewith (which may be provided as separate modules or as an omnibus program) embedded therein and/or executable by and/or one or more Application Specific Integrated Circuits (ASICs), for programmatically directing and/or performing certain described actions, operations or method steps. The circuit can reside in one location or multiple locations, it may be integrated into one component or may be distributed, e.g., it may reside entirely in a workstation or single computer, partially in one workstation, cabinet, or computer, or partially or totally in a remote location away from a local display at a workstation. If the latter, a local computer and/or processor can communicate over a LAN, WAN and/or internet to transmit, for example, a service access code to remotely "unlock" the locked housing or to provide the code to allow a user or operator to unlock and open a locked housing, or to send an alert of an operational fault to a user via the system display, or a mobile communication device such as a cellular telephone, PDA, electronic tablet or notepad or other portable or non-portable computer.

The term "automatically" means that the operation can be substantially, and typically entirely, carried out without human or manual input, and is typically programmatically directed or carried out. The term "electronically" includes both wireless and wired connections between components. The term "about" means that the recited parameter or value can vary by between about +/−20%.

Figure 1B:
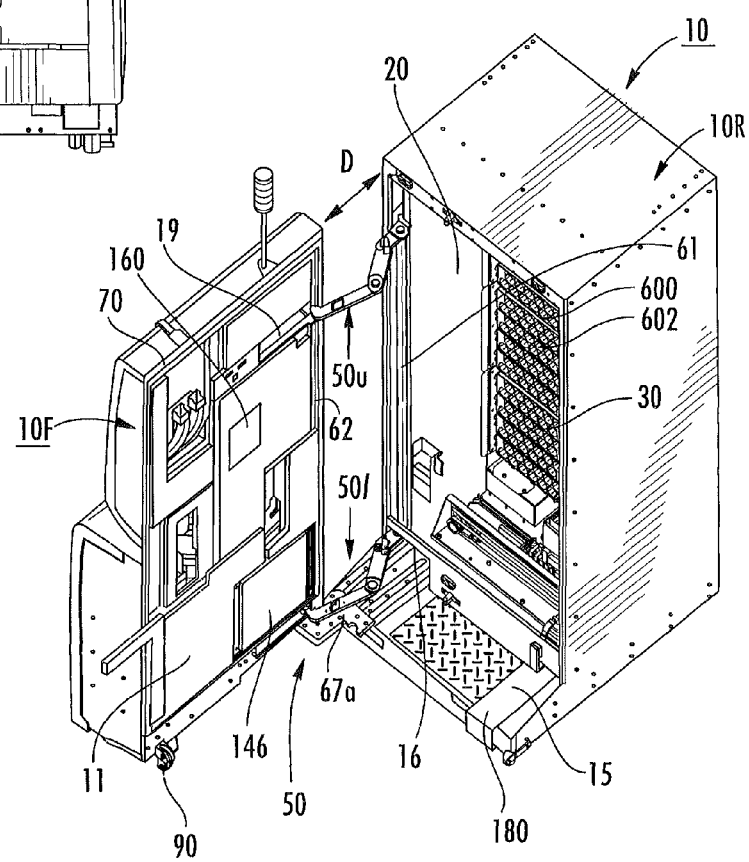
FIG. 1B is a top perspective view of the housing of FIG. 1A showing the front and rear housing members open with a separation distance "D" according to embodiments of the present invention.
Figure 1C:
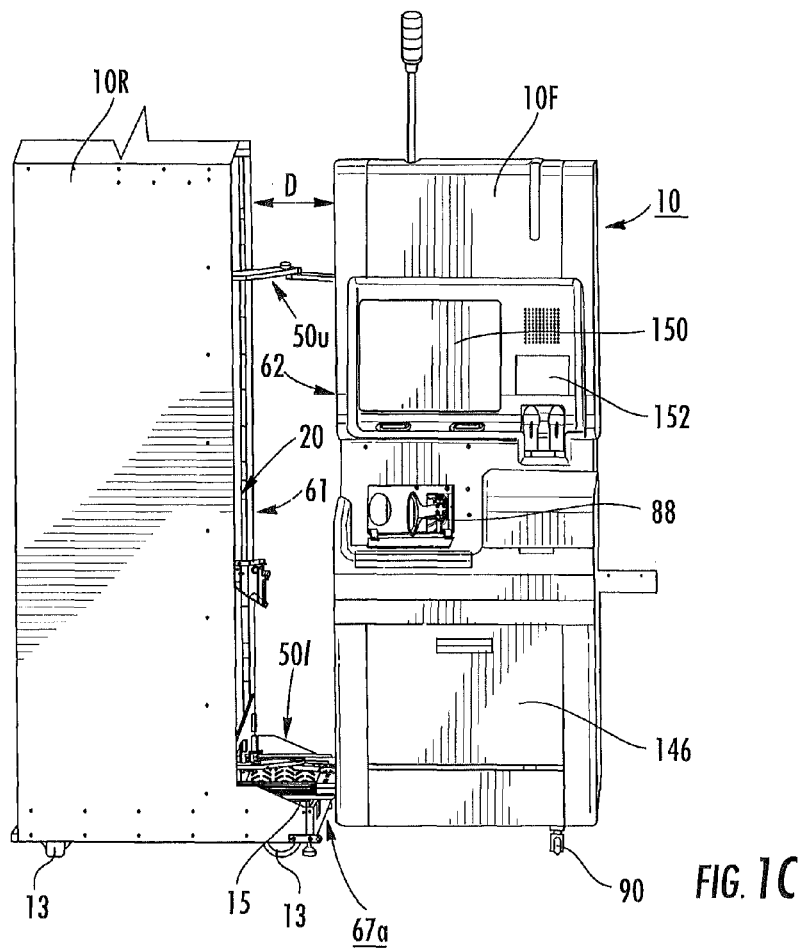
FIG. 1C is a left side view of the housing shown in FIG. 1B illustrating the front housing extending out a distance "D" from the rear housing according to embodiments of the present invention.

Referring now to the figures, FIGS. 1A-1C illustrate a housing 10 with front and back housing members 10F, 10R, respectively, that open to allow access to an interior cavity 20 of the housing. The housing 10 also includes a hinge assembly 50a that is attached to both the front and back housing members 10F, 10R to allow the front housing member 10F to slide straight outward a distance "D," then pivot open to allow access to the interior cavity. 20. The hinge assembly 50 typically includes upper and lower hinge assemblies, 50u, 50l as shown.

FIGS. 1B and 1C illustrate the gap distance "D" between the front and rear housing members 10F, 10R that is provided by sliding the front housing member 10F out this distance, before allowing the front housing member 10F to pivot. This allows the front member 10F to be positioned with a clearance from contact with an adjacent instrument (see, e.g., FIG. 11) and/or provides a relatively wide field of view and access to the interior cavities of both of the housing members 10F, 10R. The front housing member 10F can slide outwardly the distance "D" with its front housing front and rear walls remaining substantially horizontal. The distance "D" can be between about 2-12 inches, typically between about 4-10 and any value therebetween including about 4 inches, about 5 inches, about 6 inches, about 7 inches, about 8 inches, about 9 inches and about 10 inches. The rear housing member 10R can include wheels 13 that reside on a support floor of a building, typically a research or commercial laboratory facility.

The front housing member 10F can be pivoted inwardly and slid rearwardly to close the housing 10 with the front and back housing members 10F, 10R, respectively, in proper alignment. The movement can be in response to manual pushing of the front member 10F and/or via electronic control.

FIG. 1B also illustrate that the front housing member 10F can optionally include an interior service access display 160 to allow for trouble shooting interface when the front housing is open and the primary display 150 (FIG. 2) is on the opposing side (the user would need to look around the front while working in back).

Figure 1D:
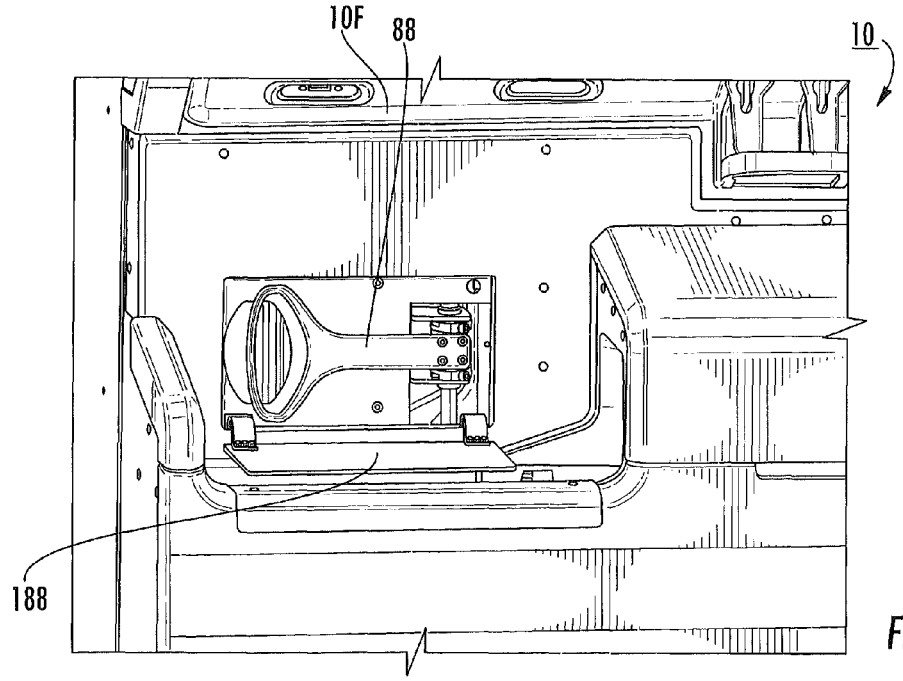
FIG. 1D is a greatly enlarged view of a front portion of the housing shown in FIG. 1A.

FIGS. 1A, 1C-1F illustrate that in some particular embodiments, a front access lever (e.g., handle) 88 may be provided to allow a user to open the housing 10. FIG. 1D illustrates that the lever 88 may reside inside a flat access panel 188. The lever 88 can be rotated out to turn one or more locks 288, shown as two locks 288u, 288l, one on a top and one on a bottom portion of the front housing member 10F, each connected to the lever 88 via shaft 189. When the lever 88 is pulled and/or rotated outwardly from the housing 10, it rotates the shaft 189 which turns the locks 288, causing them to disengage the perimeter of the rear housing member 10R. Other embodiments can employ electronic locks or other lock configurations.

The front and back housing members 10F, 10R can be configured to sealably engage to provide a climate controlled chamber 30 in the interior cavity 20. The back housing member 10R can be configured to remain substantially stationary as the hinge mechanism extends to open the housing 10. The front housing member 10F and the rear housing member 10R can be relatively heavy, typically at least about 50 pounds, or at least about 100 pounds, and, in some embodiments, at least about 200 pounds. The housing 10 can open to provide the user access to the interior at the back of the rear housing member 10R which can enclose drive systems, robot mechanisms, agitation assemblies and other automated processing equipment. The hinge mechanism 50 can allow the housing 10 to open for cleaning, container access, and jam clearing with relatively minimal manual effort and typically without requiring disruption of operation of an adjacent apparatus. As shown in FIGS. 1B and 1C, while the front housing member 10F is open, the rear 11 of the front member 10F is also accessible for service. The rear housing member 10R can have an interior volume that is larger than that of the front housing member 10F (typically at least three times the volume). In some embodiments, the rear housing member 10R can have a front base portion 15 that resides a distance above a support floor or a room and under the lower hinge assembly 50l.

Figure 2:
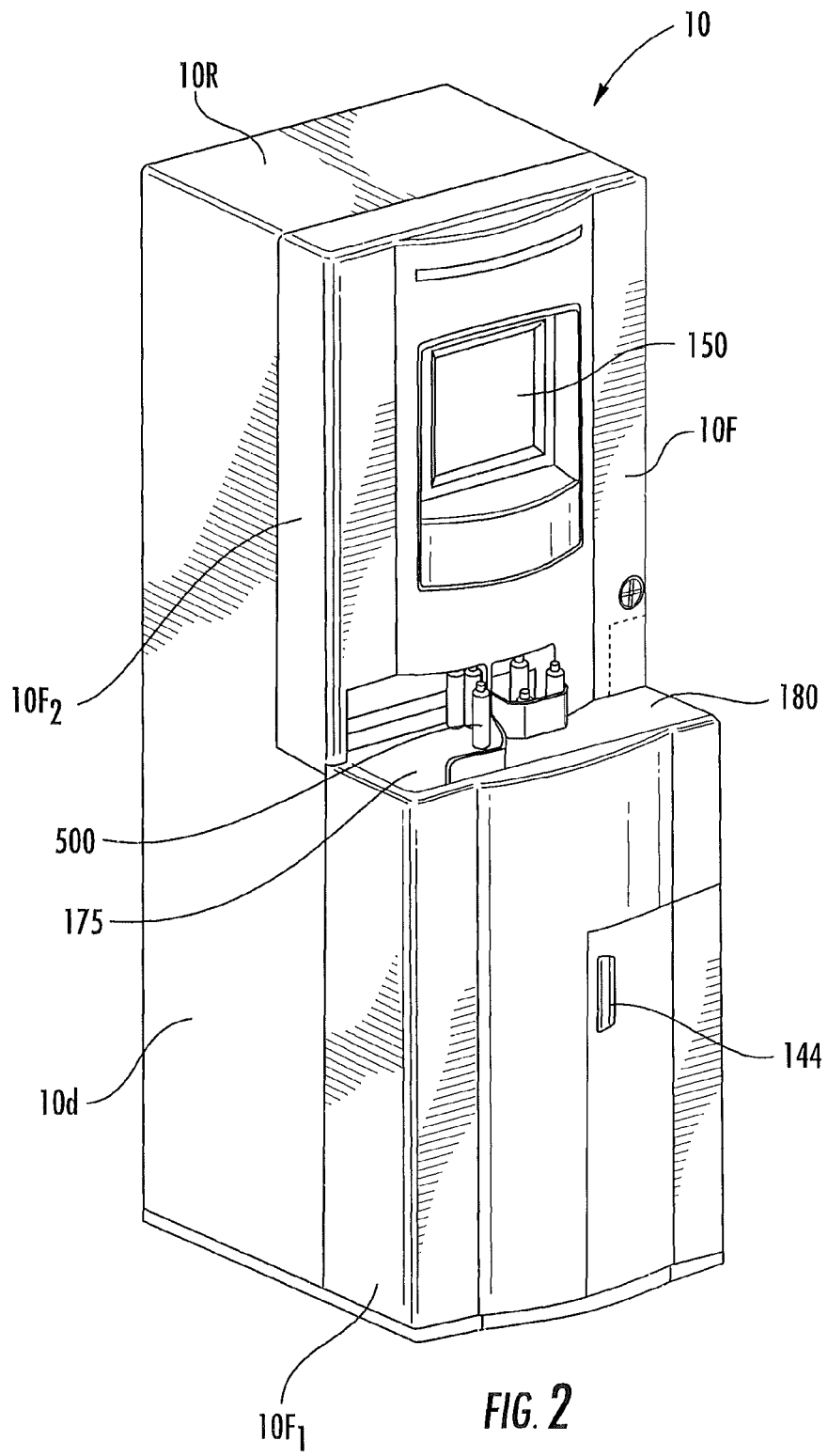
FIG. 2 is a side perspective view of another housing illustrating that the front housing member can have upper and lower portions that may be opened together or separately to allow access to an interior of the housing according to embodiments of the present invention.

In the embodiment shown in FIGS. 1B and 1C, there are two cooperating hinge mechanisms 50, an upper one 50u at an upper portion of the housing 10 and a lower one 50l at a lower portion of the housing 10 along a common side of the housing. However, the housing 10 may also include a single mechanism 50 or more than two hinge mechanisms. Also, as shown in FIG. 2, it is contemplated that the front housing member 10F can be provided as a multi-component structure, such as a housing member having a bottom portion $10F_1$ and a top portion $10F_2$ that could each separately open and one or both of which could include at least one hinge mechanism 50.

Figure 8:
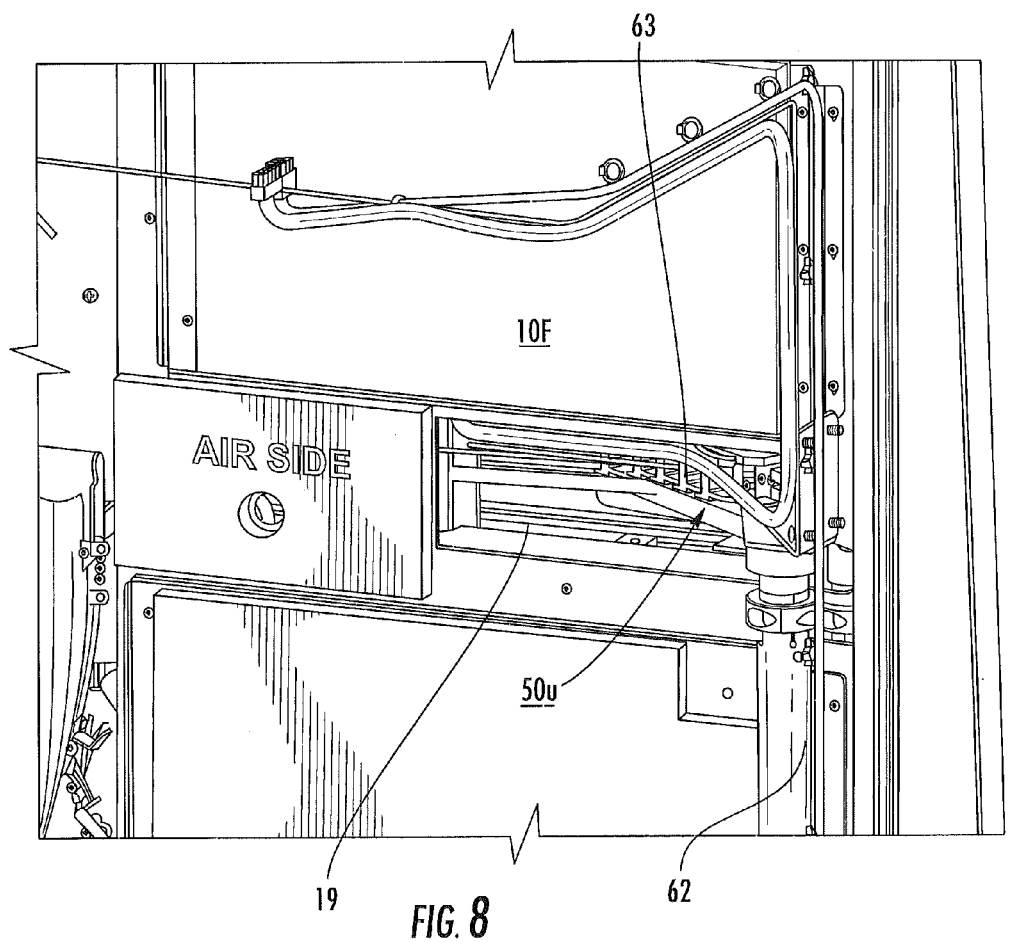
FIG. 8 is an enlarged partial view of an interior side of the front housing members shown in FIG. 1B according to embodiments of the invention.

FIGS. 1B, 1C and 4A-4C illustrate that each hinge mechanism 50u, 50l includes a mechanical linkage assembly 50a that includes first and second linkages 51, 52 pivotably attached together at a respective adjacent first end portion via attachment member 53. One linkage 51, 52 can overlie the other when closed (FIG. 8).

Figure 3A:
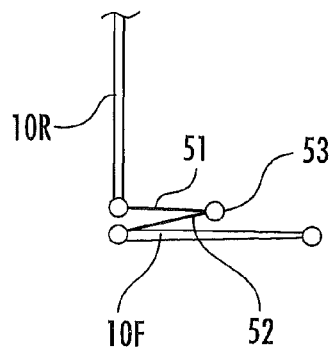
FIGS. 3A-3D are schematic illustrations of sequential configurations of front and rear housing members as the housing is opened using a sliding hinge assembly according to embodiments of the present invention.
Figure 3B:
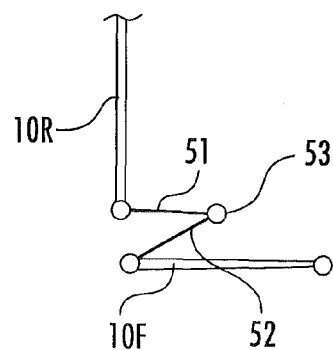
Figure 3C:
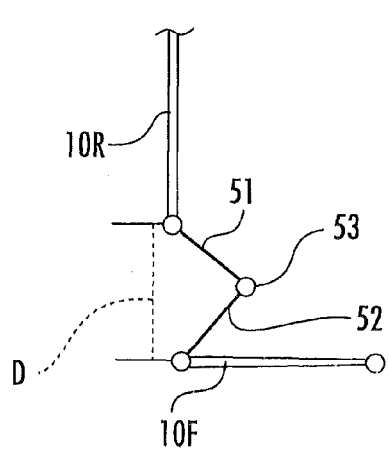
Figure 3D:
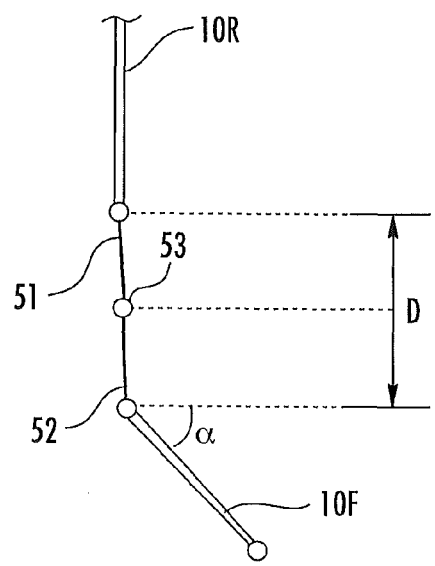

FIGS. 3A-3D schematically illustrate an exemplary sequence of different configurations that the front and rear housing members 10F, 10R can have as the housing moves from a closed position to an open configuration. As shown, the hinge assembly linkages 51, 52 are adjacent to each other when the housing is closed (FIG. 3A) and the front housing member 10F moves straight out a distance "D" as shown in FIGS. 3B and 3C before the front housing member 10F is allowed to pivot open to an angle "a", typically between about 60-120 degrees, more typically between about 80-100 degrees, such as about 80 degrees, about 85 degrees, about 90 degrees, about 95 degrees, and about 100 degrees (see, e.g., FIGS. 1B, 1C).

As shown, each linkage assembly 50a is a two-bar linkage, but other linkages can be used. Also, the upper mechanism 50u can have a different linkage configuration and different numbers of links than the bottom linkage assembly 50l. One or more of the linkages 51, 52 in a linkage assembly 50a can include cable carriers 63 that are attached to cables 120 (FIGS. 4B, 4C) such as power and/or data cables that extend between components in the front of the housing 10F (e.g., from a display with a User Interface) and components in the rear of the housing 10R (e.g., a power supply) and allow for flex movement of the cables 120 in and out, that avoids pinch points, in response to opening and closing the hinge mechanism 50. The linkages 51, 52 can include attachment members 63c such as clamps that hold the cable carriers 63. The cable carriers 63 can comprise Igus® cable carriers. The cable carrier attachment members 63c can reside on upper surfaces of the top and bottom first and second linkages 51, 52 to locate Igus® tracks for the cables to pivot in and out.

Referring to FIGS. 1B, 1C, 4A, 4B, 4C and 5A, for example, the housing 10 can include downwardly extending hinge rods 61, 62 that connect the top and bottom hinge mechanisms 50u, 50l together. The first linkage 51 can be attached at the end portion away from the pivot 53 to the rear housing member 10R and/or hinge rod 61. The second linkage 52 can be attached at an opposing end portion from the pivot 53 to the front housing member 10F and/or hinge rod 62.

FIGS. 1B, 4B and 4C, for example, show that the linkages 51, 52 can act as a scissor-type mechanism to extend and retract, and when extended can lock the hinge rods 61, 62 together. The hinge rods 61, 62 can reside facing each other proximate a common edge portion of the housing 10 so that each is enclosed in the housing 10, when closed. As the hinge mechanisms 50u, 50l slide open to separate the front and back housing members 10F, 10R, the rods 61, 62 can cause the upper and lower hinge linkages 50u, 50l to slide open in concert.

FIG. 4B shows the top mechanism 50u can be clamped into place using an adjustment clamp 65 for longitudinal adjustment. This clamp 65 allows adjustments to be made so that the front and rear housing members 10F, 10R are aligned when closed. The bottom mechanism 50l can be assembled to be fixed into the longitudinal position.

Referring to FIGS. 4C and 5A-5C, the lower hinge mechanism 50l can be in communication with a linear slide assembly 67a. The linear slide assembly 67a can include an upper member 67 that cooperates with a lower member 167 to define a linear slide track for the front housing member 10F.

Figure 6A:
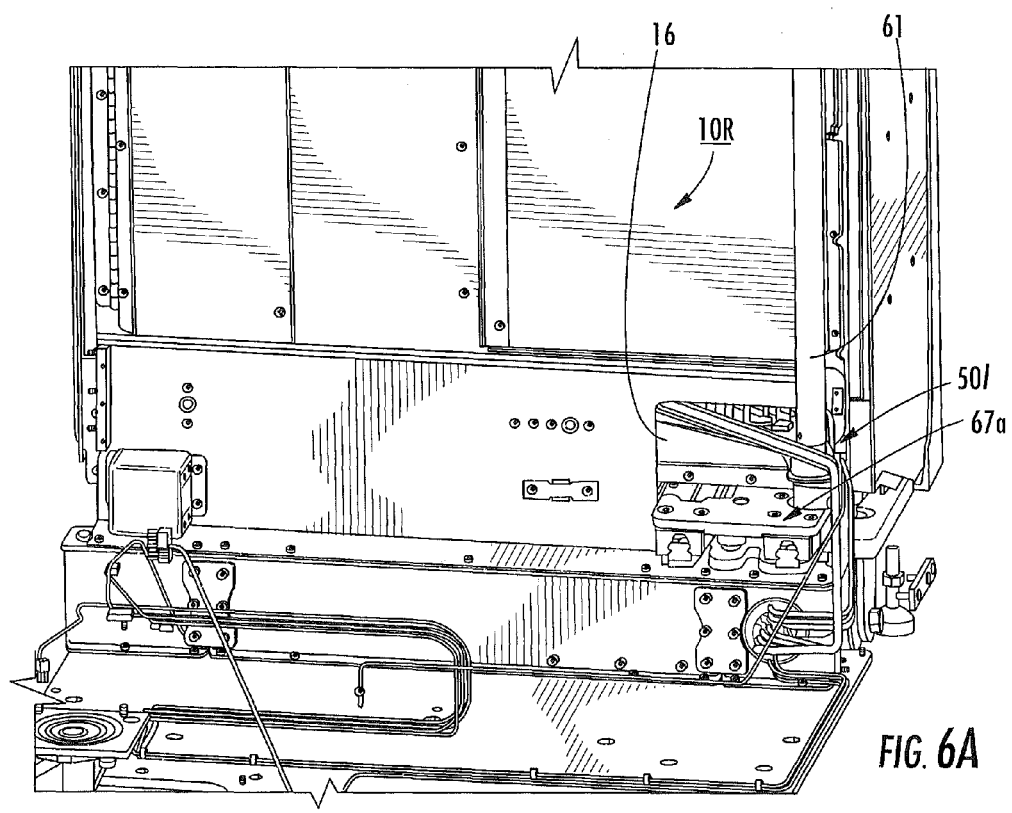
FIG. 6A is a front perspective view of the lower hinge assembly and linear slide assembly according to embodiments of the present invention.
Figure 6B:
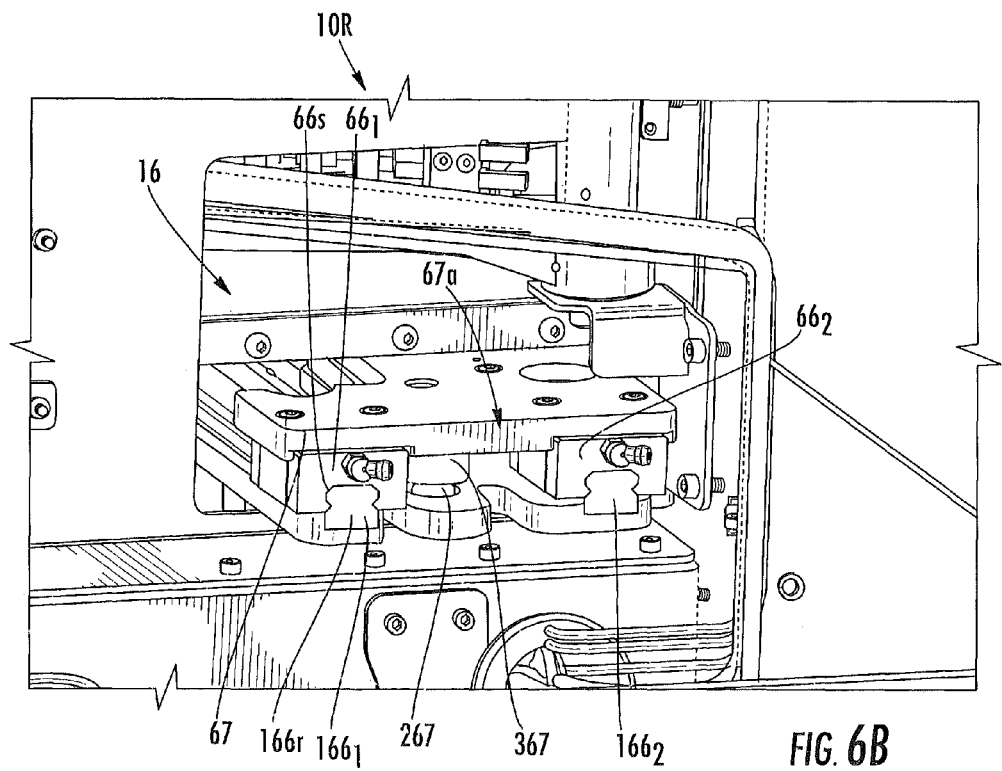
FIG. 6B is an enlarged front perspective view of the lower hinge assembly and linear slide assembly shown in FIG. 6A.
Figure 7:
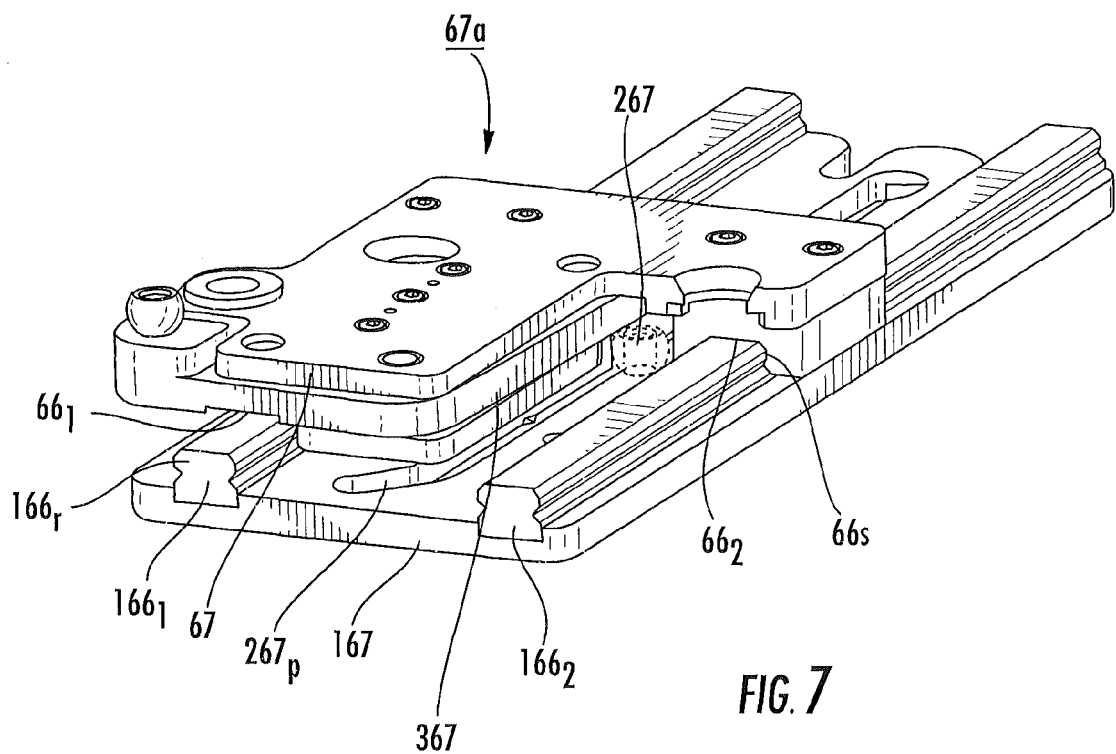
FIG. 7 is a front perspective view of the linear slide assembly showing the front housing cam and slide rails according to embodiments of the present invention.

Referring to FIGS. 6A, 6B and 7, the upper and lower members 67, 167 can each be configured as plates of rigid substrates that are horizontally oriented. FIGS. 6B and 7 show that the lower member 167 can define slots or rails 166r (e.g., side by side rails $166_1$, $166_2$) that engage with rails or slots 66s ($66_1$, $66_2$) on the upper member 67. These respective cooperating-features define linear "slides". As shown, the upper member 67 includes downwardly extending first and second rails $66_1$, $66_2$ that slide along corresponding parallel slots $166_1$, $166_2$ in the lower member 167 to carry the load of the front housing member 10F as it slides forwardly and pivots. However, the lower bottom plate 167 can have upstanding rails $166_1$, $166_2$ and the cooperating slides $66_1$, $66_2$ have downwardly-extending slots. Combinations of the different slide configurations may also be used, e.g., one upper rail with a cooperating lower slot as one slide and one upper slot with a cooperating lower rail as another slide.

The first linear slide $66_1$ and $166_1$ can be spaced apart a small distance, such as between about 1-5 inches, for example, from the second linear slide $66_2$, $166_2$. In other embodiments a single slide, or more than two slides, can be used.

Figure 5A:
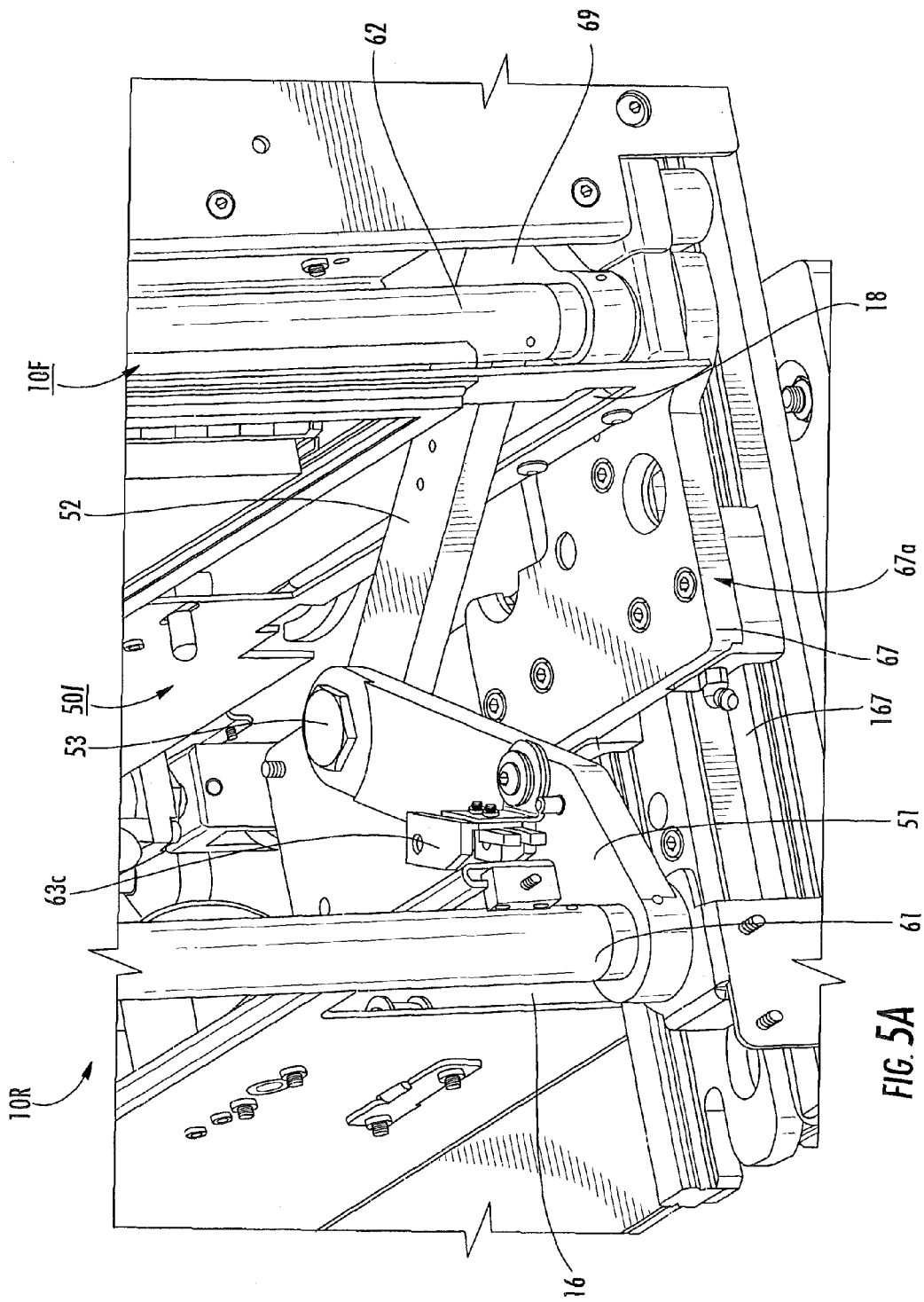
FIGS. 5A-5C are enlarged perspective views of the lower hinge shown in FIGS. 1B and 1C according to embodiments of the present invention.
Figure 5B:
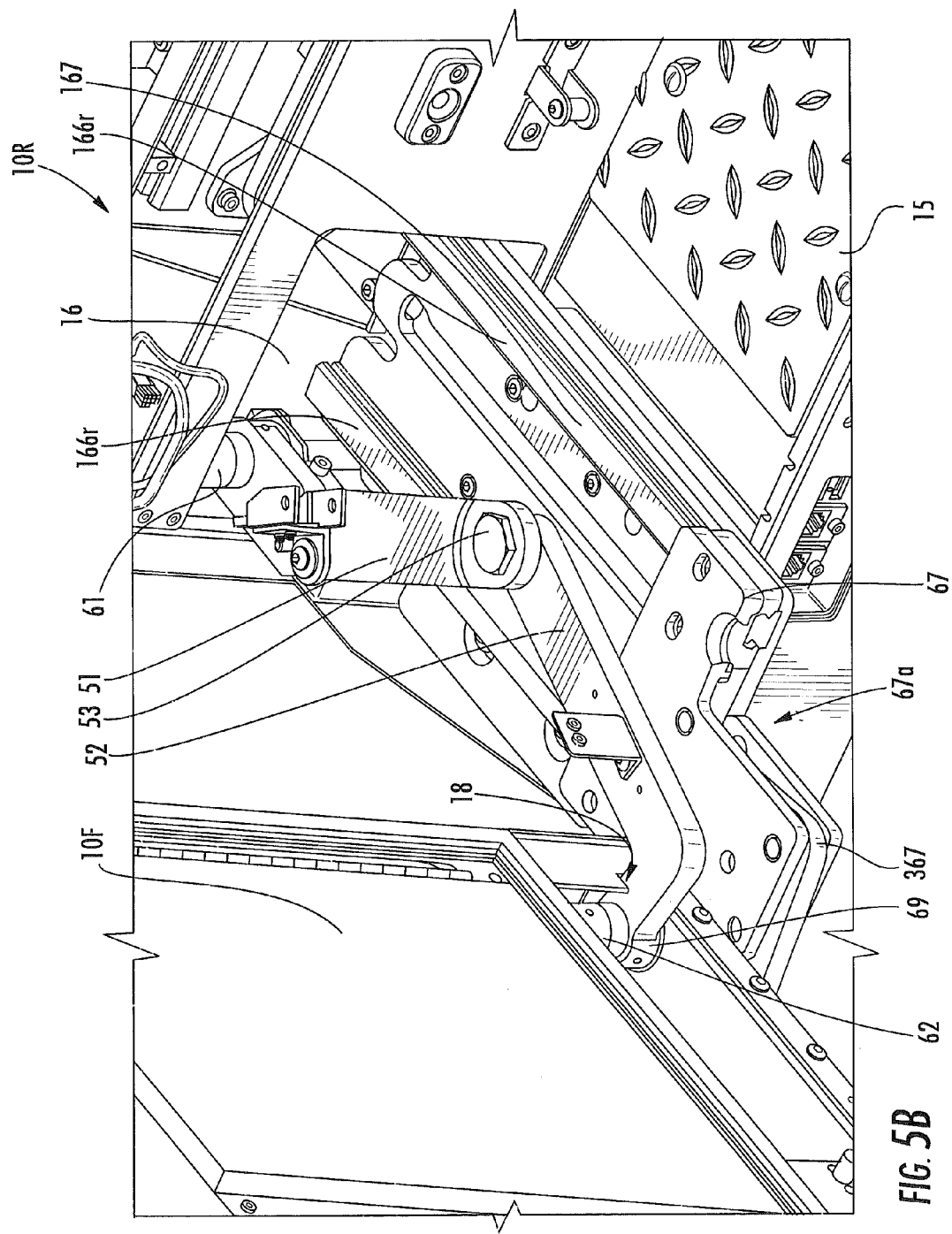
Figure 5C:
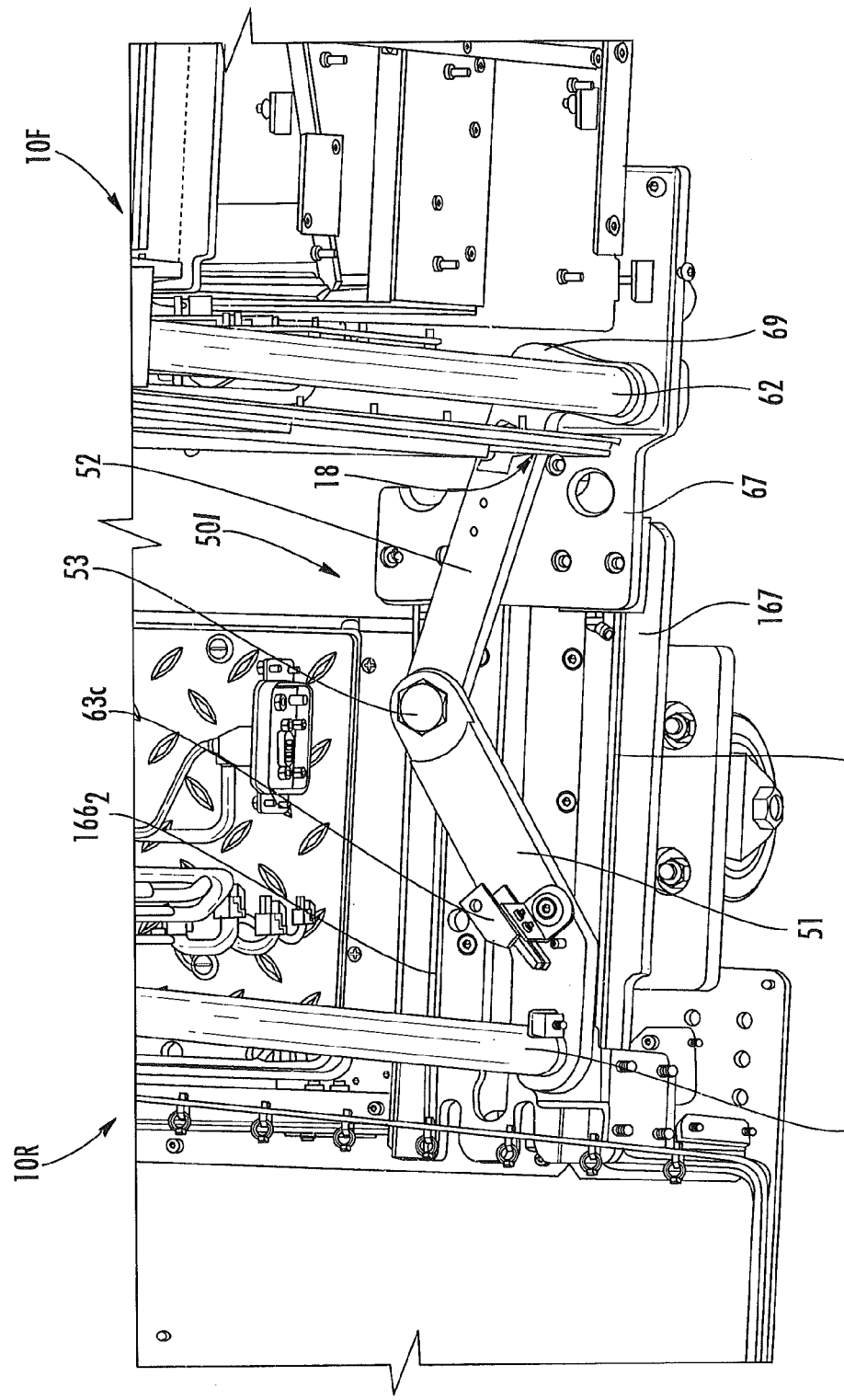

The linear slide assembly 67a can include a small linear ball joint 267 that defines/controls the motion of a cam 367 positioned between the upper and lower members 67, 167 (FIG. 7). The cam 367 can include a curvilinear path 267p for the ball 267 to define a ball joint for the pivot action of the front door about rod 62. FIGS. 5A-5C illustrate that the lower mechanism linkage 52 can be attached to the rod 62 and can include an end portion 69 that extends outward a distance beyond the rod 62 to reside in an open space 18 (slot, groove or other opening) in a bottom portion of the front housing member 10F. The linkage end portion 69 and linear slide assembly 67a are configured to prevent the front housing member 10F from pivoting until the linear slide assembly 67a slides out a specified distance "D", e.g., between about 2-12 inches, typically between about 4-10 inches such as about 8 inches as noted above.

FIG. 5B illustrates that the linear slide assembly 67a can include a cam or intermediate pivot plate 267, sandwiched between the plates 67, 167. As the upper plate/member 67 slides a defined distance out from the lower member 167, the intermediate plate 267 can pivot. The pivot plate 267 can include a curvilinear cam path 267p. The pivot plate 267 can pivot to allow the front member 10F to pivot. The rod 62 in the front housing member (e.g., "door") 10F pivots with the pivot plate 267 and the rod 61 in the back housing member 10R pivots with the two-bar linkage 51, 52.

Referring to FIGS. 5A-5D, in operation, the front housing member 10F slides straight forwardly on slides $66_1$, $66_2$, and $166_1$, $166_2$ a distance "D" to clear adjacent instruments before pivoting open to an angle "a" that is typically between about 60-120 degrees, more typically between about 60-100 degrees, and in some embodiments between about 85-90 degrees, and in some particular embodiments about 80 degrees (relative to its closed position). This allows the back housing member 10R to provide structural integrity and maintain a wider wheel base for improved stability. The guide rails/slots $166_1$, $166_2$ allow the front housing member 10F to slide out with minimal effort while eliminating pinch points and contact with adjacent instruments. Power and data lines 120 can be connected to the linkages 51, 52 which allows them to slide in and out at a distance above the floor. When fully extended, the distance "D" and links 51 and 52 may be aligned in a straight line as shown in FIG. 5D. Alternatively, the links 51 and 52 may be angled with respect to each other (not shown).

As shown in FIGS. 5B, 6A and 6B, the rear housing member 10R can include a lower pocket 16 for receiving the hinge mechanism 50l when the housing is closed. FIG. 8 shows that the front housing member 10F can include an upper pocket 19 that receives the upper hinge assembly 50u when the housing is closed. These pockets 16, 19 may include thermal insulation, such as about 0.5 inch layers of thermal padding on inner walls, to reduce air flow and provide more efficient thermal operation for climate controlled chambers. The thermal padding may comprise Hushcloth® acoustical foam and/or insulation wrap material.

FIGS. 1B and 1C, for example, show that the rear housing member 10R may also include a lower shelf 15 with the lower hinge mechanism 50l residing close to or supported by an upper surface of the shelf 15.

Referring to FIGS. 1A-1C and FIGS. 9A-9F, in some embodiments, particularly for cantilevered front housing members 10F that may be relatively heavy that do not include floor support wheels, the front housing member 10F can include a manually or automatically deployable kick stand 90. The kick stand 90 can inhibit sagging due to the cantilevered door when open and/or provide stabilization if someone leans on the front housing member 10F while extended.

Figure 9A:
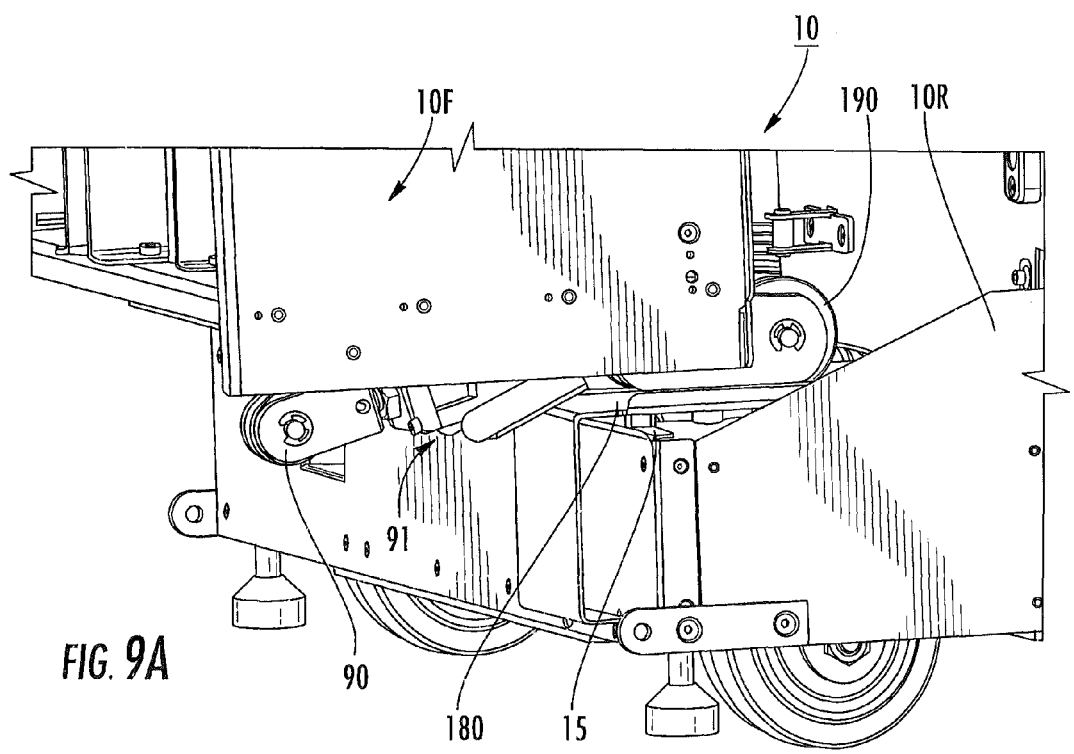
FIG. 9A is a rear perspective view of a kick stand assembly having a guide wheel and a kick stand wheel according to embodiments of the present invention.
Figure 9B:
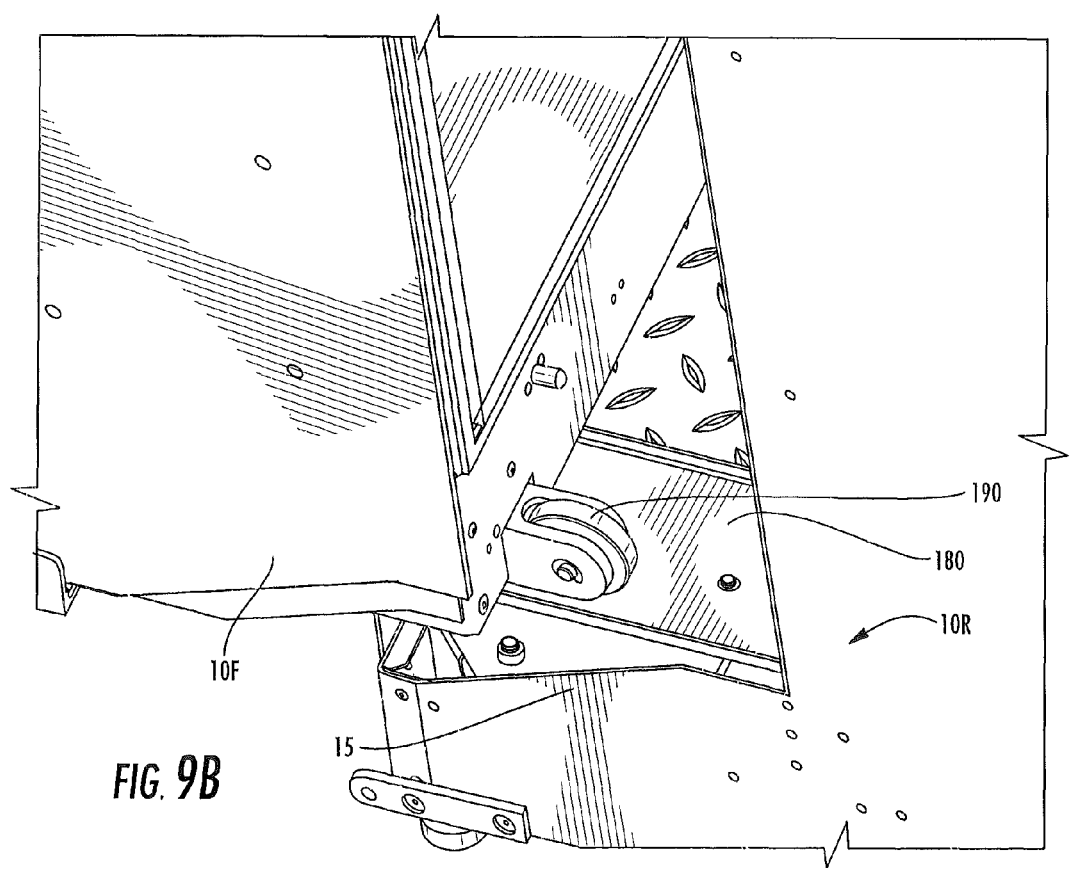
FIG. 9B is a top perspective view of the kick stand assembly shown in FIG. 9A.
Figure 9C:
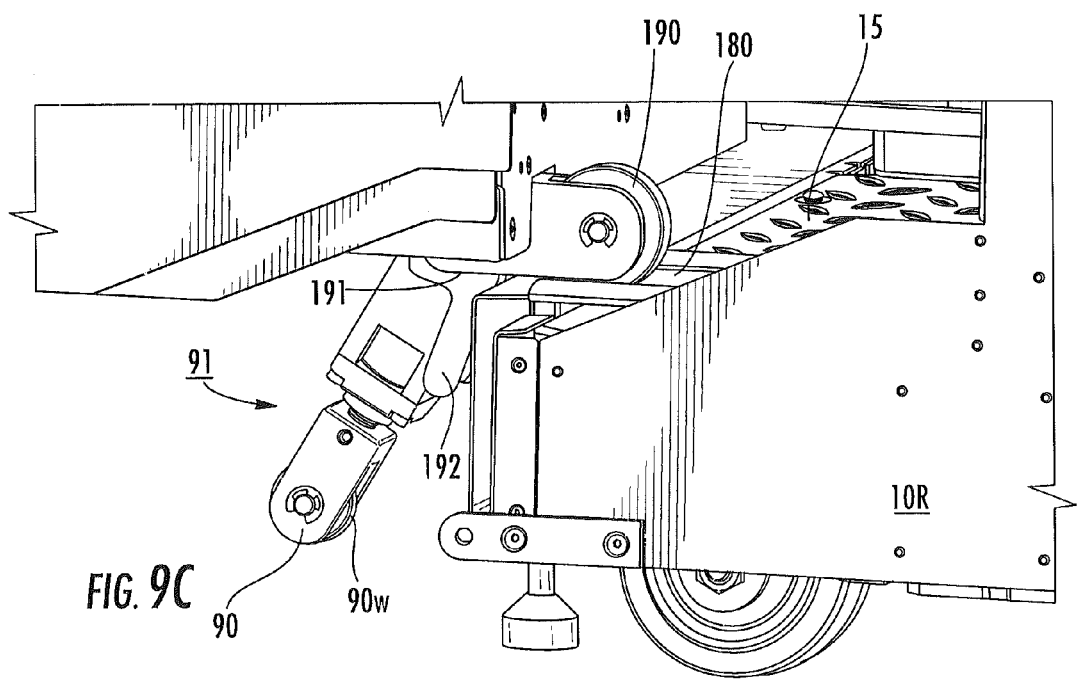
FIG. 9C is a side perspective view of the kick stand assembly shown in FIGS. 9A and 9B, illustrating that as the front housing member opens, the kick stand drops downwardly according to embodiments of the present invention.
Figure 9D:
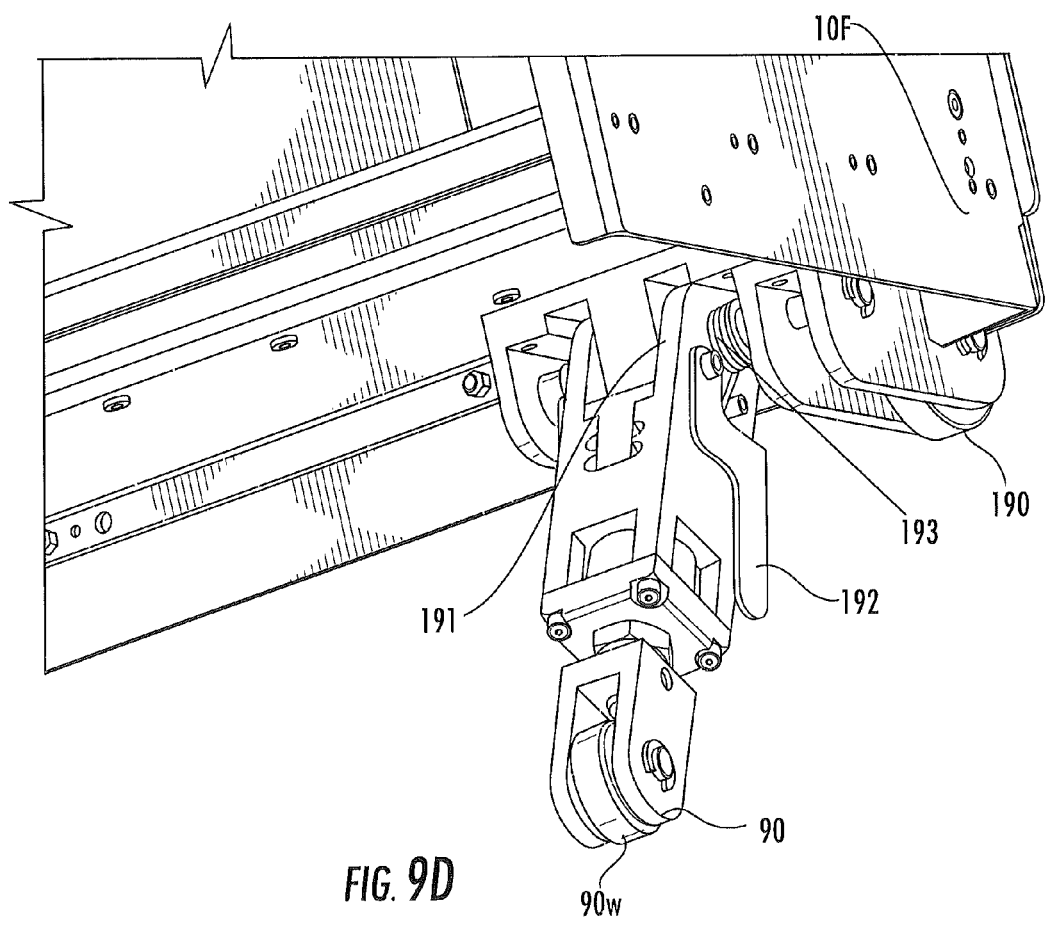
FIG. 9D is a front, side perspective view of the kick stand assembly shown in FIG. 9C.
Figure 9E:
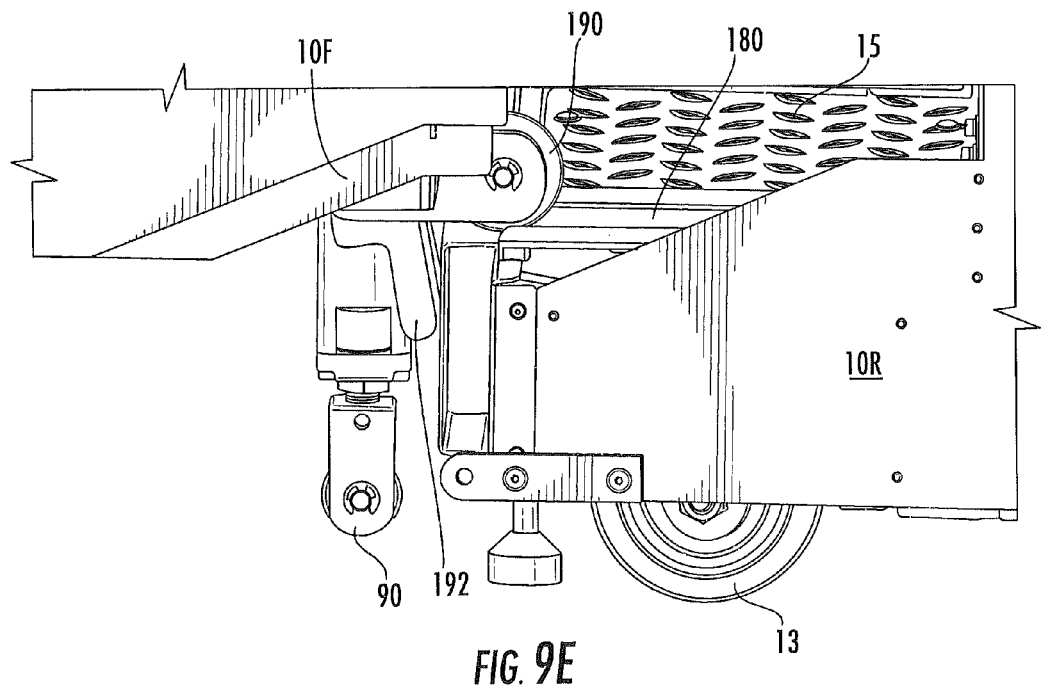
FIG. 9E illustrates the kick stand deployed vertically downwardly and ready to support a weight of the front housing member according to embodiments of the present invention.
Figure 9F:
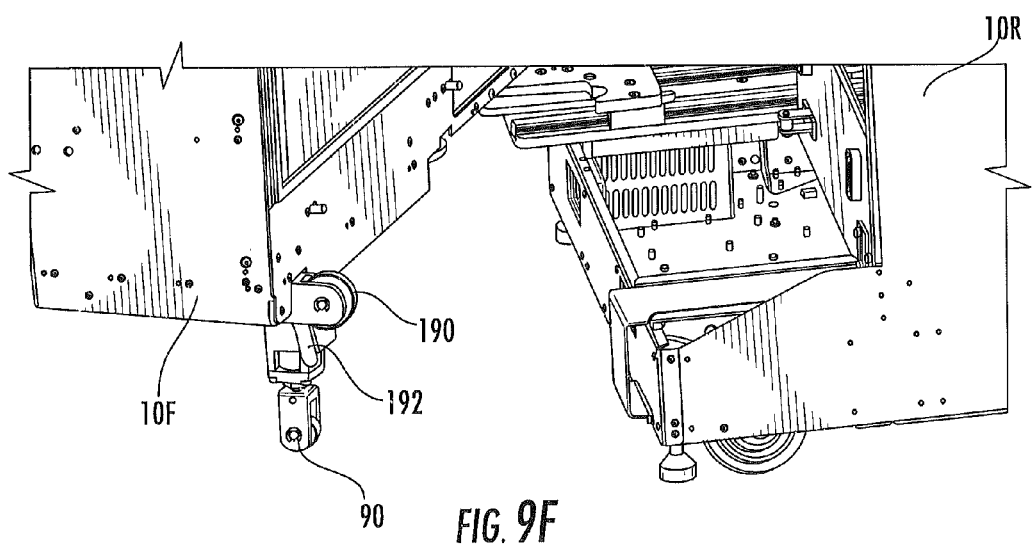
FIG. 9F is a side perspective view of the kick stand supporting the front housing member when the front housing member is open a distance away from the rear housing member according to embodiments of the present invention.

In some embodiments, the kick stand 90 is spring-loaded 193 and can automatically rotate down into place from a stowed configuration as the front housing member 10F opens to help support the weight of the housing member 10F, Referring to FIGS. 9A-9F, in some embodiments, the kick stand assembly 91 is attached to a lower portion of a rear portion of the front housing member 10F and can include a front wheel 90w that is part of the kick stand 90 that is in communication with a rear wheel 190. The rear wheel 190 can be supported by and move forwardly over a floor surface 180 on the base 15 of the rear housing member 10R as the front housing member 10F slides forwardly to open the housing 10. FIG. 9A illustrates the kick stand assembly 91 when the housing 10 is almost closed. FIGS. 9C-9E show the downward movement of the kick stand 90 as the front housing member 10F moves away from the rear housing member 10R, which moves the wheel 190 forwardly, which moves the kick stand 90 down to its vertical support configuration shown in FIG. 9F. The kick stand 90 can be pivotably attached to the front housing member via pivot 191 and can be spring-loaded 193 to be biased to extend downwardly when the rear wheel is free of the base 15 of the rear housing 10R. The kick stand assembly 91 can include a spring plate 192 that spans a body portion of the kick stand. In reverse, as the wheel 190 contacts surface 180, the spring plate 192 is forced upwardly, which, in turn, forces the kick stand 90 upwardly to thereby draws the kick stand upward to its stow configuration.

Figure 11:
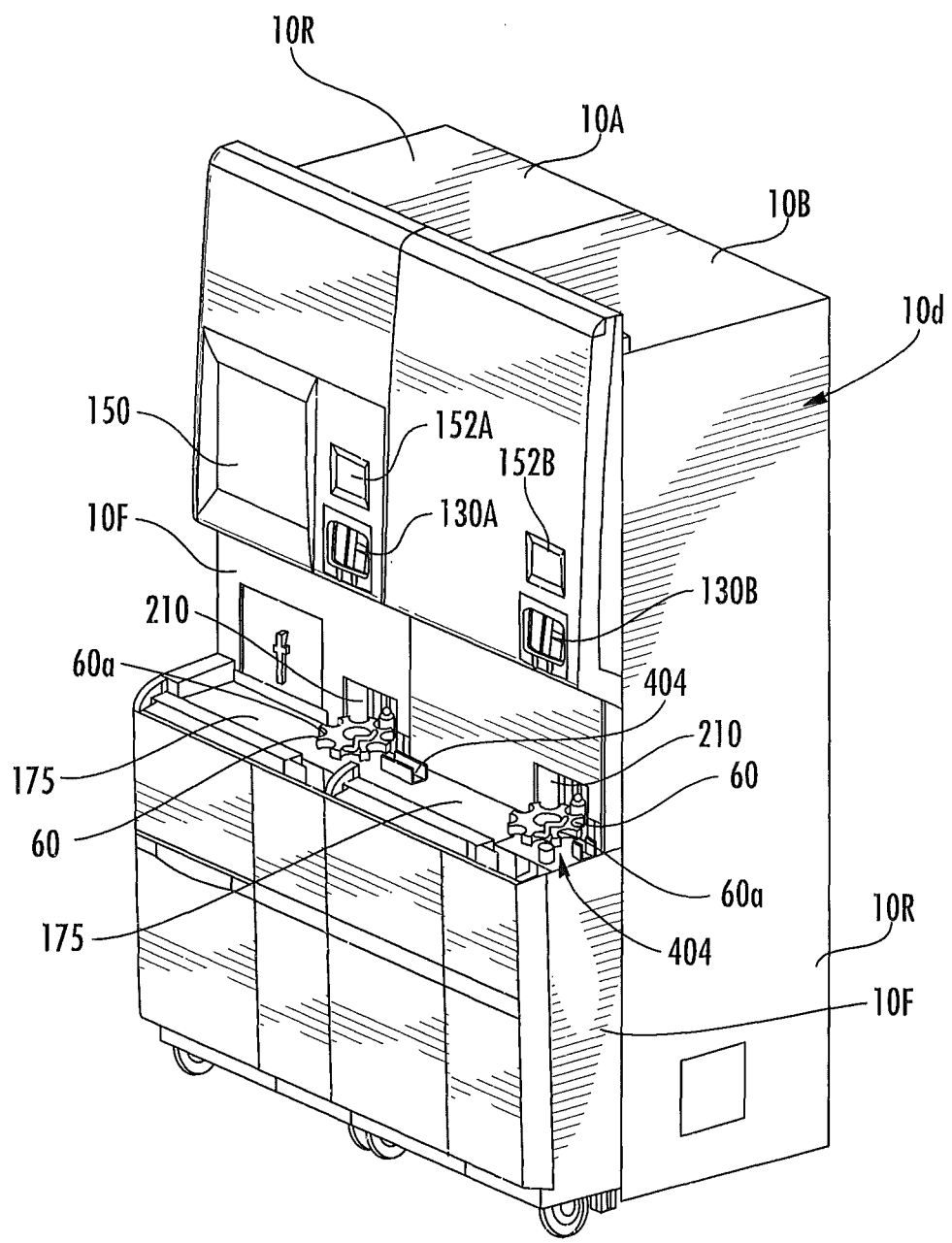
FIG. 11 is a front perspective view of an example of automated detection systems according to embodiments of the present invention.
Figure 12:
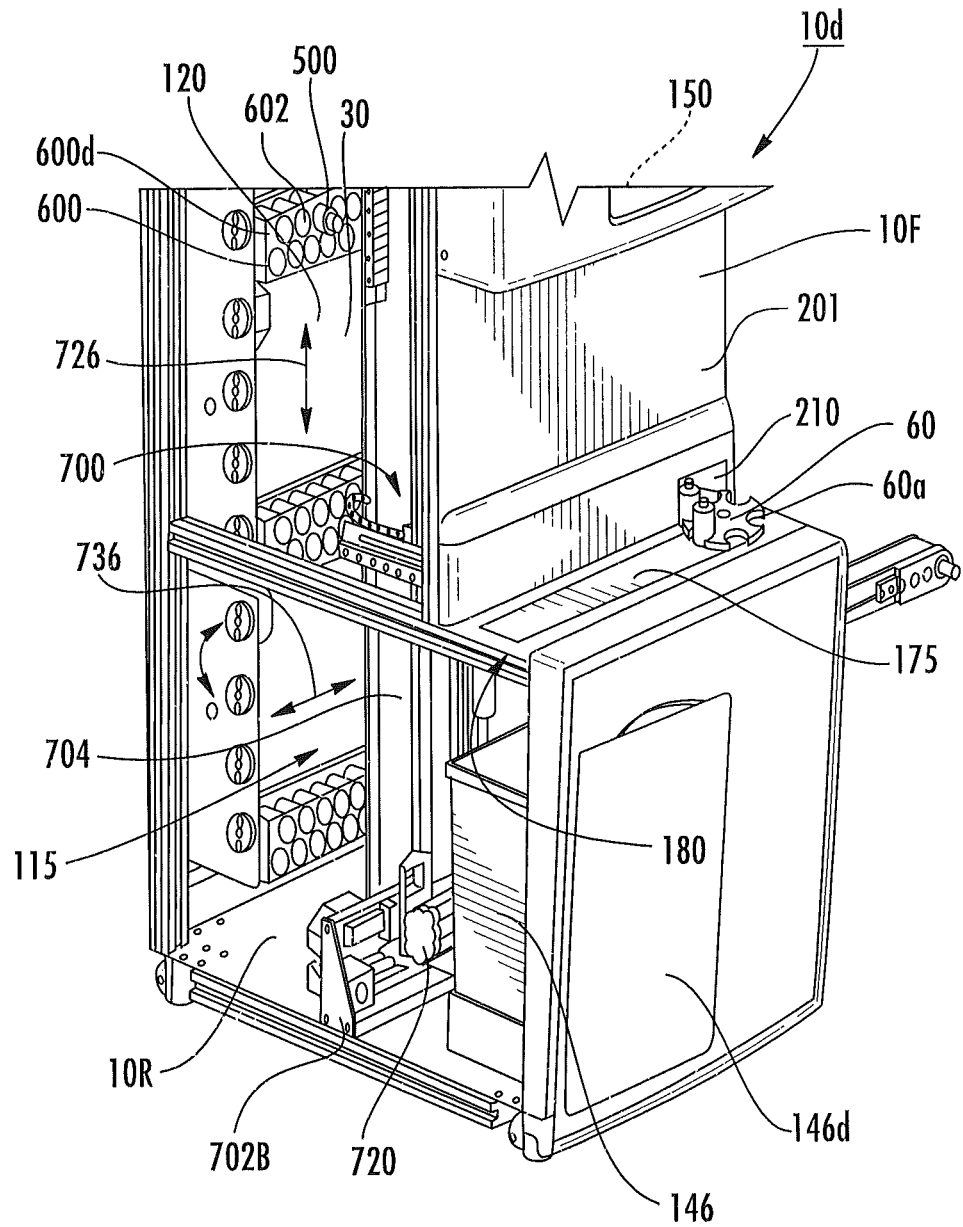
FIG. 12 is a partial cutaway view of an example of an automated detection system according to embodiments of the present invention.

The housing 10 can be a floor standing instrument with internal operating components generally divided to reside in one of the front housing member or the rear housing member, 10F, 10R. For example, for an automated microorganism detection system, Robot, Agitation, and Thermal Assemblies can be in the rear housing member 10R and Container Loader, Waste, and User Interface Assemblies can be in the front having member 10F. Multiple microorganism detection systems can be connected together to provide a single loading area. Access to all areas of the instrument can be through the front of the instrument when the front housing member 10F is open. As shown in FIGS. 1A and 1B, as the interior cavity in the back of the housing 10R can contain a climate controlled incubation region, the housing 10 can include an air seal 70 between the front and back housing members 10F, 10R, FIGS. 11 and 12 illustrate a housing 10 that defines an automated microbial (microorganism) detection apparatus 10d. The apparatus 10d can include a display 150, an external conveyor 175 and index wheel 60 that loads containers 500 into a port 210 for loading into an incubation rack inside a climate controlled chamber 30 in the housing 10, FIG. 2 also shows that the front housing member 10F can include a top portion 10F$_2$ and a bottom portion 10F$_1$ as noted above with respect to FIG. 2. The top portion 10F$_2$ can slide open and pivot out using one or more of mechanism 50u, 50l which would leave the conveyor (loader) system 175 intact. Alternatively, as shown in FIG. 11, the conveyor system 175 can be part of a single piece front housing member 10F that slides, then pivots open.

While embodiments of the invention are particularly suitable for automated microbe detection systems, the designs may be used on other instruments for ease or service access and/or reduced footprint requirements, including those devices that have adjacent instruments or structure and/or instruments connected to each other such as chemical analysers or instruments that are part of a conveyor system.

The housing 10 can optionally include a lock that inhibits an unauthorized user from opening the housing 10. In some embodiments, no lock is used, but a controller 100 (FIG. 10) can disable operation of internal components, such as a robotic arm or drive system, if data from an on-board sensor associated with either or both the front and back housing members 10F, 10R indicates that the housing 10 is being opened or is open. The sensor can be a position sensor such as a Hall-Effect sensor.

Figure 10:
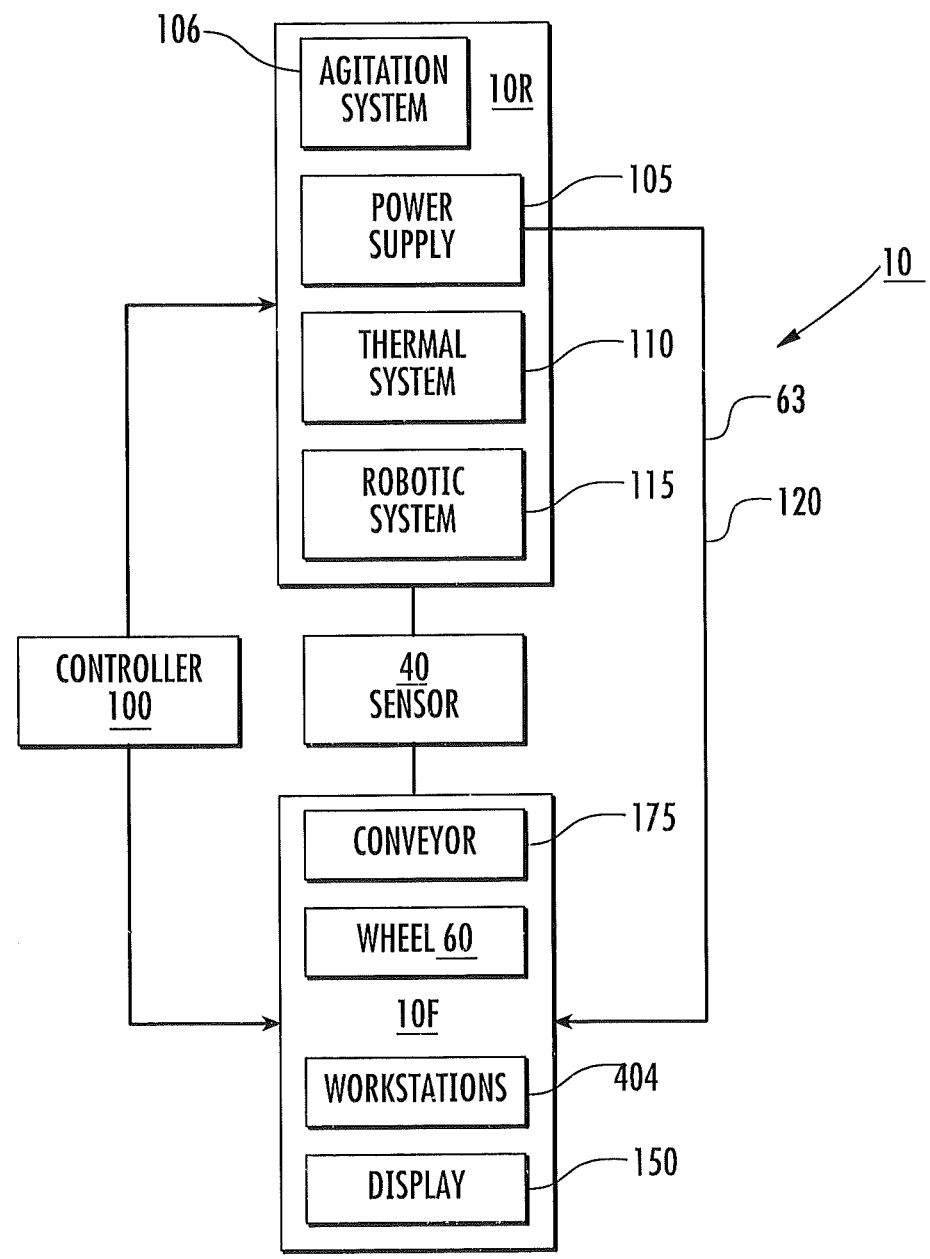
FIG. 10 is a block diagram of an automated detection system according to embodiments of the present invention.

Referring to FIG. 10, the housing 10 can hold various components in the front housing member 10F and various components in the rear housing member 10R, including a power supply 105, typically at a lower portion of the rear housing member 10R. Power and data lines 120 can extend between components held in the front and back housing members 10F, 10R, and can be routed between the front and back housing members 10F, 10R with flexible cable carriers 63 (e.g., Igus® cable carriers) supported by the linkages 51, 52. The rear housing member 10R may also include a thermal system 110 (e.g., heating elements, blowers and the like), a robotic system 115, and an agitation system 106 (including motors and drives that operate the robotic system 115) to place containers in various racks 600 with container stations 602 (FIGS. 1A, 12) and agitate the containers using movement or vibration and the like. The front housing member 10F can hold a conveyor 175, an index wheel 60, various workstations 404 in communication with the wheel 60 and the display 150, all of which can be powered by the power supply 105. The controller 100 can reside in either the front or rear housing members 10F, 10R and may be distributed in each or even reside partially or totally in a remote location(s) and communicate with the components using a LAN, WAN or the Internet.

As noted above, in some embodiments, the housing 10 can define an automated apparatus such as an automated microbe detection system 10d shown in FIGS. 11 and 12 for automated detection of a microbial agent (e.g., a microorganism) that may be present in a test sample or specimen sample. In general, any known test sample (e.g., a biological sample or specimen) can be used. For example, the test sample can be a clinical or non-clinical sample suspected of containing one or more microbial agents. Biosamples, such as a bodily fluid, include, but are not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, blood products (e.g., platelets, serum, plasma, white blood cell fractions, etc.), donor organ or tissue samples, and the like. In one embodiment, the biological sample tested is a blood sample. Other samples that may be tested include, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, and fruit) and bio-warfare samples.

As shown, for example, in FIGS. 2, 11 and 12, the automated detection system 10d can include an external conveyor 175 and index wheel 60 with container receiving pockets or receptacles 60a. The interior cavity 20 holds a climate-controlled chamber 30 (e.g., a temperature-controlled incubation chamber wherein the temperature is maintained at approximately 37 degrees Celsius) to promote or enhance microbial growth. As shown in FIGS. 11 and 12, the housing 10 also may include a first port or container entrance location 210 and a user interface display 150. However, as one of skill in the art would appreciate, other design configurations are possible.

The term "index" with reference to the word "wheel" means that the wheel can be configured to repeatedly start, then stop to move a defined distance as a respective pocket 60a rotates about a rotational cycle to serially present respective adjacent pockets at a loading position. This indexing can be used to present loaded pockets to one or more downstream processing stations proximate an outer perimeter portion of the wheel 60 away from the container intake or loading position. In some embodiments, a respective container 500 can be rotated through a series of defined workstations such as an electronic reading and/or weighing station, then to an intake port to serially move the containers 500 into the housing 10 for further processing, such as, by way of example, for incubation in a climate controlled chamber, then for analysis by an automated analyzer for microbial growth and/or other defined parameters.

In the embodiment shown in FIGS. 11 and 12, a larger lower section of the housing supports an externally accessible shelf 180 that provides a user workstation and/or workflow access points to the detection system 10d. The shelf 180 may hold the conveyor 175 and wheel 60.

In operation, a user or technician (or an automated input mechanism such as a robotic arm or side feed conveyor) can place one or more specimen containers 500 onto a container loading station or area. The conveyor 175 or other transport mechanism can transport the specimen containers 500, typically upright and in gross, to the wheel 60, and subsequently into the housing 10 of the detection system 10d, thereby loading the container into the system. FIG. 12 shows that the detection system 10d can be a single housing with a single interior chamber 30 while FIG. 11 shows two side-by-side housings 10A, 10B with respective conveyors 175 and wheels 60 for processing containers 500 into different input ports 210 then into respective racks 600.

As shown for example in FIG. 11, the automated detection system 10d may contain one or more work-flow stations 404 for obtaining one or more measurements, readings, scans and/or images of a specimen container, thereby providing information such as container type, container lot number, container expiration date, patient information, sample type, test type, fill level, weight measurement, etc. Furthermore, the one or more work-flow stations 404 may comprise one or more container management stations, such as a container pick-up station or a container transfer station. For example, the automated detection system 10d may contain one or more of the following work-flow stations 404: (1) a bar code reading station; (2) a container scanning stations; (3) a container imaging station; (4) a container weighing station; (5) a container pick-up station; and/or (6) a container transfer station. In operation, the wheel 60 indexes to locate a specimen container 500 to one or more work-flow stations 404 positioned about the perimeter of the wheel. In some embodiments, one or more of the work-flow stations 404 are included within the housing 10 of the detection system 10d.

FIG. 11 also illustrates that the wheel 60 can define a plurality of receiving pockets 60a which can include vertically spaced apart upper and lower planar substrates with an open gap space therebetween. The rotatable wheel 60 contains one or more receiving pockets 60a, for example, between 1 to 20, typically between about 4-10, such as 4, 5, 6, 7, 8, 9 or 10. In operation, the wheel 60 rotates (either clockwise or counterclockwise) in a horizontal plane (and around or about a vertical axis) to move an individual container 500 to or among various work-flow stations 404 (i.e., from station-to-station). In some embodiments, the work-flow station 404 is operable to obtain one or more measurements or readings of the specimen container, thereby providing information about the container, such as, container lot number, container expiration date, patient information, sample type, fill level, etc. In some embodiments, one or more of these measurements and/or readings can occur at the same station. For example, container weight, scanning, imaging and/or pick-up may occur at a single station location.

As shown in FIG. 12, in some embodiments, the detection system 10d will also include a detector 600d for detecting growth (e.g., a detection unit) in the specimen containers 500. In general, any detector configuration or type for detecting microbial growth in a container can be used. For example, as is well known in the art, each holding station or rack 600 may contain horizontal pockets 602 and a linear scanning optical system that has the capability of non-invasive monitoring of microorganism growth in each specimen container 500. In one embodiment, the optical system detector 600d can interrogate a sensor (e.g., a Liquid Emulsion Sensor (LES) sensor) in the containers 500, thereby detecting microorganism growth within the container.

In general, any known detection system for monitoring and/or interrogating a specimen container for the detection of microbial growth can be used. As previously mentioned, the specimen containers 500 can be monitored continuously, or periodically; during incubation of the containers 500 in the detection system 10d, for the positive detection of microbial growth. For example, in one embodiment, a detection unit 600d reads the sensor incorporated into a bottom portion or base of the container 500. A variety of sensor technologies are available in the art and may suitable. In one possible embodiment, the detection unit takes colorimetric measurements as described in the U.S. Pat. Nos. 4,945,060; 5,094,955; 5,162,229; 5,164,796; 5,217,876; 5,795,773; and/or 5,856,175, which are incorporated herein. A positive container is indicated depending upon these colorimetric measurements, as explained in these patents. Alternatively, detection could also be accomplished using intrinsic fluorescence of the microorganism, and/or detection of changes in the optical scattering of the media (as disclosed, for example, in co-pending U.S. patent application Ser. No. 12/460,607, filed Jul. 22, 2009 and entitled, "Method and System for Detection and/or Characterization of a Biological Particle in a Sample"). In yet another embodiment, detection can be accomplished by detecting or, sensing the generation of volatile organic compounds in the media or headspace of the container. Various design configurations for the detection unit can be employed within the detection system. For example, one detection unit could be provided for an entire rack or tray, or multiple detection units could be provided per rack or per tray.

The specimen container 500 is shown in the form of a standard culture bottle (e.g., a blood culture bottle). However, the description of a culture bottle (e.g., a blood culture bottle) is offered by way of example and not limitation. The container 500 may include a bar code label for automated reading of the container 500. In some embodiments, the top portion of the container 500 can include a narrow portion or neck. The container 500 also includes a cap (e.g., a stopper) optionally having a pierceable septum and may also have a sensor (e.g., an LES sensor) formed or placed in the bottom portion of the container 500 for purposes of colorimetric detection of the presence of microbial growth in the container 500. The container 500 can include a body with an optically transmissive material. The container 500 may further comprise a growth or culture medium (not shown) for promoting and/or enhancing microbial or microorganism growth. The use of a growth or culture media (or medium) for the cultivation of microorganisms is well known. A suitable growth or culture medium provides the proper nutritional and environmental conditions for growth of microorganisms and should contain all of the nutrients required by the microorganism which is to be cultivated in the specimen container 500. After a sufficient time interval to allow amplification of microorganisms (this time interval varies from species to species), the container 500 can be tested within the detection system 10*d* for the presence of microbial or microorganism growth. The testing may occur continuously or on a periodic basis so that the container can be determined as positive for microorganism growth as soon as possible.

As shown, for example in FIG. 12, the automated detection system 10*d* may further comprise an automated mechanism 700 operable for the transfer of a specimen container 500 for container management within the system. As the containers 500 accumulate in the entrance location or port 210, the containers 500 are moved within the detection system 10*d* whereby a transfer mechanism 700 (e.g., a robotic system 115 with a transfer arm with a container grip mechanism) can pick up, or otherwise receive, an individual specimen container 500 and transfer and place that container into a holding structure or rack 600 within the detection system 10*d*. As known in the art, the mechanism may use a vision system (e.g., camera), pre-programmed dimensional coordinates and/or precision motion controlling to transfer a specimen container 500 to, and load the specimen container into, the holding structure or rack 600.

In accordance with one embodiment, the containers 500 are placed or held in a plurality of holding structures or racks 600, and optionally agitated to enhance microorganism growth therein. As shown for example in FIG. 12, the receiving structures or wells 602 of the holding structures or racks 600 can be orientated along a horizontal axis. Accordingly, in accordance with this embodiment, the automated transfer mechanism 700 re-orientates the containers 500, from a vertical orientation to a horizontal orientation, during the transfer of the container 500 from the wheel 60 to the holding members/rack wells 602.

In some embodiments, the transfer mechanism 700 can operate to remove or unload "positive" and "negative" containers from the holding structures or racks 600. This automated unloading mechanism can operate to ensure that once a "positive" or "negative" reading has been made for each specimen container 500, the container 500 is removed from the container receiving structures or well 602, making room for another container to be loaded into the detection system 10*d*, thereby increasing system through put.

In some embodiments, the transfer mechanism 700 comprise a robotic transfer arm. In general, any type of robotic transfer arm known in the art can be used. For example, the robotic transfer arm can be a multi-axis robotic arm (for example, a 2-, 3-, 4-, 5-, or 6-axis robotic arm). The robotic transfer arm can operate to pick up and transfer a specimen container 500 (e.g., a blood culture bottle) from an entrance location or port 210 to one of a plurality of container receiving structures or wells 602 located in one of a plurality of holding structures or racks 600 (optionally having an agitation assembly). Furthermore, to facilitate the movements of the transfer mechanism or robotic transfer arm, the interior chamber 30 of the detection system 10*d* may include one or more supports for the robotic transfer arm. For example, one or more vertical supports and/or one or more horizontal supports may be provided. The transfer mechanism or robotic transfer arm can slide up and down and across the supports as necessary to access any of the receiving structures or wells 602 of the holding structures or racks 600.

In yet another embodiment, the robotic transfer arm may include one or more devices for obtaining measurements, scans and/or readings of a specimen container 500. For example, the robotic transfer arm may include one or more video cameras, sensors, scanners, and/or bar code readers. In accordance with this embodiment, the video camera, sensor, scanner and/or bar code reader may aid in container location, reading of container labels (e.g., bar codes), container scanning, remote field servicing of the system, and/or detecting for any possible container leaks within the system. In yet another design possibility, the robotic transfer arm may include a UV light source to aid in automated decontamination, if necessary.

The transfer mechanism robotic transfer arm 700 can include one or more horizontal support structures 702B, one or more vertical support structures 704, and a robotic head that will include one or more features or devices (e.g., a gripping mechanism) to pick-up, grip and/or hold a specimen container 500. The robotic head can be supported by, coupled to, and/or attached to one of the horizontal supports and/or vertical supports. For example, as shown in FIG. 12, the robotic transfer arm 700 comprises a lower horizontal support structure 702B and a single vertical support structure 704. Although not shown, as one of skill in the art would appreciate, an upper horizontal support structure or other similar means can be used to further support or guide the vertical support structure. In general, any known means in the art can be used to move the robotic head up and down relative to the vertical support rail 704 (as represented by arrow 726), and move the vertical support rail 704 back-and-forth along the horizontal support structure(s) 702B (as represented by arrow 736). The robotic transfer arm 700 may further comprise a vertical drive motor 720 and vertical drive belt that can operate to transfer or move the robotic head up and down (arrow 726) the vertical support rail 704 to transfer or move a container 500 along (i.e., up and down) a vertical axis (i.e., the y-axis). Accordingly, the vertical support structure 704, vertical guide rail 728, vertical drive motor 720 and vertical drive belt allow the robotic transfer arm 700 to move or transfer the robotic head and a specimen container 500 along the y-axis. The robotic transfer arm 700 may further comprise a first horizontal drive motor, first horizontal drive belt and horizontal guide rail that will operate to move the vertical support structure 704 back-and-forth (i.e., from left-to-right and/or from right-to-left) along the horizontal guide rail, and thus, along a first horizontal axis (i.e., the x-axis) within the housing 201 of the detection system 10*d* (see arrow 736). Accordingly, the robotic transfer arm 700 move or transfer a specimen container 500 along the x-axis. The automated robotic transfer arm 700 can be placed under the control of a system controller (100, FIG. 10) and programmed for specimen container 500 management (e.g., pick-up, transfer, placement and/or container removal) within the detection system 10*d*.

As shown in FIGS. 1B, 12, there can be a plurality of vertically stacked container holding structures or racks 600, each having a multitude of specimen container receiving structures or wells 602, each for holding individual specimen containers 500 inside chamber 20. Each individual holding structure or rack 600 can comprise two or more container receiving structures of wells 602. For example, each holding structure or rack 600 can comprise from about 2 to about 40, from about 2 to about 30, or from about 2 to about 20 receiving structures of wells 602 therein. In one embodiment, as shown in FIG. 12, the racks 600 can comprise two rows of vertically aligned receiving structures or wells 602. In an alternative embodiment, the receiving structures or wells 602 can be staggered, thus reducing the vertical height of each individual holding structure or rack 600, thereby allowing for an increased number of total holding structures or racks 600 in a given vertical distance within the incubation chamber 20.

Furthermore, each of the individual container receiving structures or wells 602 typically has a specific X and Y coordinate position or address, where X is the horizontal location and Y is the vertical location of each container receiving structure or well 602. The individual wells 602 are accessed by a transfer mechanism, such as a robotic transfer arm 700, for example, as described hereinabove. The automated transfer mechanism 700 can operate to move the robotic head with a respective specimen container 500, to a specific one of the X, Y positions in the rack 600 and deposit the container 500 therein. In operation, the automated transfer mechanism 700 can operate to pick up a specimen container 500 at the entrance station 210 or other pick-up station, move a container 500 determined positive for microbial growth therein to a positive container or exit location and/or to move a container 500 determined negative for microbial growth to a negative container location or waste bin 146 (FIG. 12). The waste bin 146 may reside inside a drawer or door 146*d* so as to allow a user ease of access to empty the waste bin 146 as desired.

In some embodiments, the entire holding structure or rack 600 can be agitated by an agitation assembly/system 106 (FIG. 10) to promote or enhance microorganism growth. The agitation assembly can be any known means or mechanism for providing agitation (e.g., a back-and-forth rocking motion) to the holding structures or racks 600. In another embodiment, the holding structures or racks 600 can be rocked in a back-and-forth motion for agitation of the fluid contained within the containers. For example, the holding structures or racks 600 can be rocked back-and-forth from a substantially vertical position to a substantially horizontal position, and repeated to provide agitation of the fluid contained within the container. In yet another embodiment, the holding structures or racks 600 can be rocked back-and-forth from a substantially horizontal position to a vertical position 10 degrees, 15 degrees, 30 degrees, 45 degrees or 60 degrees from horizontal, and repeated to provide fluid agitation within the containers. In one embodiment, a racking motion from a substantially horizontal position to a vertical position from about 10 degrees to about 15 degrees from horizontal may be preferred. In still another embodiment, the holding structure or racks can be rocked back-and-forth in a linear or horizontal motion to provide agitation of the fluid contained within the containers. In this embodiment, the holding structures or racks 600 and receiving structures or wells 602 can be orientated in a vertical, or alternatively in a horizontal position. These back-and-forth, liner and/or horizontal rocking motions can be repeated as desired (e.g., at various cycles and/or speeds) to provide agitation of the fluid within the containers.

As previously described, the detection system 10*d* may include a climate-controlled interior chamber (or incubation chamber) 30 for maintaining an environment to promote and/or enhance growth of any microbial agents (e.g., microorganisms) that may be present in the specimen container 500. In accordance with this embodiment, the detection system 10*d* may include a thermal system 110 (FIG. 10) with at least one heating element or hot air blower to maintain a constant defined temperature within a desired range within the interior chamber 30. For example, in one embodiment, the heating element or hot air blower will provide and/or maintain the interior chamber at an elevated temperature (i.e., a temperature elevated above room temperature). In another embodiment, the detection system thermal system 110 may include a cooling element or cold air blower (not shown) to maintain the interior chamber at a temperature below room temperature. In accordance with this embodiment, the interior chamber or incubation chamber will be at a temperature of from about 18 to about 45 degrees Celsius. In one embodiment, the interior chamber can be an incubation chamber and can be maintained at a temperature from about 35 degrees Celsius to about 40 degrees Celsius, and preferably at about 37 degrees Celsius. In another embodiment, the interior chamber may be maintained at a temperature below room temperature, for example from about 18 degrees Celsius to about 25 degrees Celsius, and preferably at about 22.5 degrees Celsius. A particular advantage provided is the ability to provide a more constant temperature environment for promoting and/or enhancing microbial growth within a specimen container 500. The detection system 10*d* can accomplish this by providing a closed system, in which automated loading, transfer and unloading of specimen containers 500 occurs without the need to open any access panels that would otherwise disrupt the incubation temperature (from about 30 to 40 degrees Celsius, preferably from about 37 degrees Celsius) of the interior chamber 30.

The detection system heating element or hot air blower can be employed in a number of locations within the interior chamber 30. For example, one or more heating elements or hot air blowers can be positioned at the base of the holding structures or racks 600, for directing warm air across the plurality of holding structures or racks 600.

The detection system 10*d* includes at least one controller 100 (e.g., a computer control system with at least one digital signal processor) (FIG. 10) and firmware for controlling the various operations and mechanisms of the system. Typically, the system controller and firmware for controlling the operation of the various mechanisms of the system can be any known conventional controller and firmware known to those of skill in the art. In one embodiment, the controller and firmware can direct all operations for controlling the various mechanisms of the system, including: automated loading, automated transfer, automated detection and/or automated unloading of specimen containers within the system. The controller and firmware can also provide for identification and tracking of specimen containers within the system.

The detection system 10*d* may also include a user interface 150 and associated computer control system for operating the loading mechanism, transfer mechanism, racks, agitation equipment, incubation apparatus, and receiving measurements from the detection units. The user interface 150 may also provide an operator or laboratory technician with status information regarding containers loaded into the detection system. The user interface may include one or more of the following features: (1) Touch screen display; (2) Keyboard on touch screen; (3) System status; (4) Positives alert; (5) Communications to other systems (DMS, LIS, BCES & other detection or identification Instruments); (6) Container or bottle status; (7) Retrieve containers or bottles; (8) Visual and audible Positive Indicator; (9) USB access (back ups and external system access); and (10) Remote Notification of Positives, System Status and Error Messages. In another embodiment, as shown in FIGS. 1 and 11, a status update screen 152 can also be used. The status update screen 152 can be used to provide status information regarding containers loaded into the detection system, such as, for example: (1) container location within the system; (2) container information, such as, patient information, sample type, input time, etc.; (3) positive or negative container alerts; (4) interior chamber temperature; and (5) an indication that the waste bin is full and needs to be emptied. FIG. 1B also illustrates the use of an optional interior service display 160 as described above.

Once a container is detected as positive, the detection system will notify the operator of the results through an indicator (e.g. visual prompt) and/or through notification at the user interface 150 or even other defined portable communication devices (remote and/or local).

As noted above, the detection system 10*d* can take on a variety of different possible configurations. One such configuration, particularly suited for high volume implementations, is for use as an automated microbiology laboratory system with one apparatus 10*d* linked or "daisy chained" to one or more additional other analytical modules or instruments for additional testing. For example, as shown in FIG. 11, the detection instrument can include a plurality of adjacent (abutting) units, such as a first detection unit 10A and a second detection unit 10B. However, in other embodiments, the detection instrument can be "daisy chained" or otherwise linked to one or more other systems or modules. These other systems or modules can include, for example, identification testing systems such as the VITEK or VIDAS systems of the assignee bioMerieux, Inc., a gram stainer, a mass spectrometry unit, a molecular diagnostic test system, a plate streaker, an automated characterization and/or identification system (as disclosed in co-pending U.S. patent application No. 60/216,339, entitled "System for Rapid Non-invasive Detection of a Microbial Agent in a Biological Sample and Identifying and/or Characterizing the Microbial Agent", which was filed May 15, 2009) or other analytical systems.

Respective containers cannot be transferred from one detection system to another in case the first one is full. A similar system transfer device may also be provided for subsequent transfer of the specimen container 500 from the second detection system 10B to a subsequent systems or modules. Further, in accordance with this embodiment, positive containers can be transferred to other systems in the automated laboratory system. For example, a container determined positive in the first detection system 10A can be transferred to the second detection system 10B and/or subsequently to an automated characterization/identification system (not shown) for automated characterization and/or identification of the microbe therein. As one of skill in the art would appreciate other possible designs or configurations for the automated laboratory system are possible and are considered part of this invention.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 13:
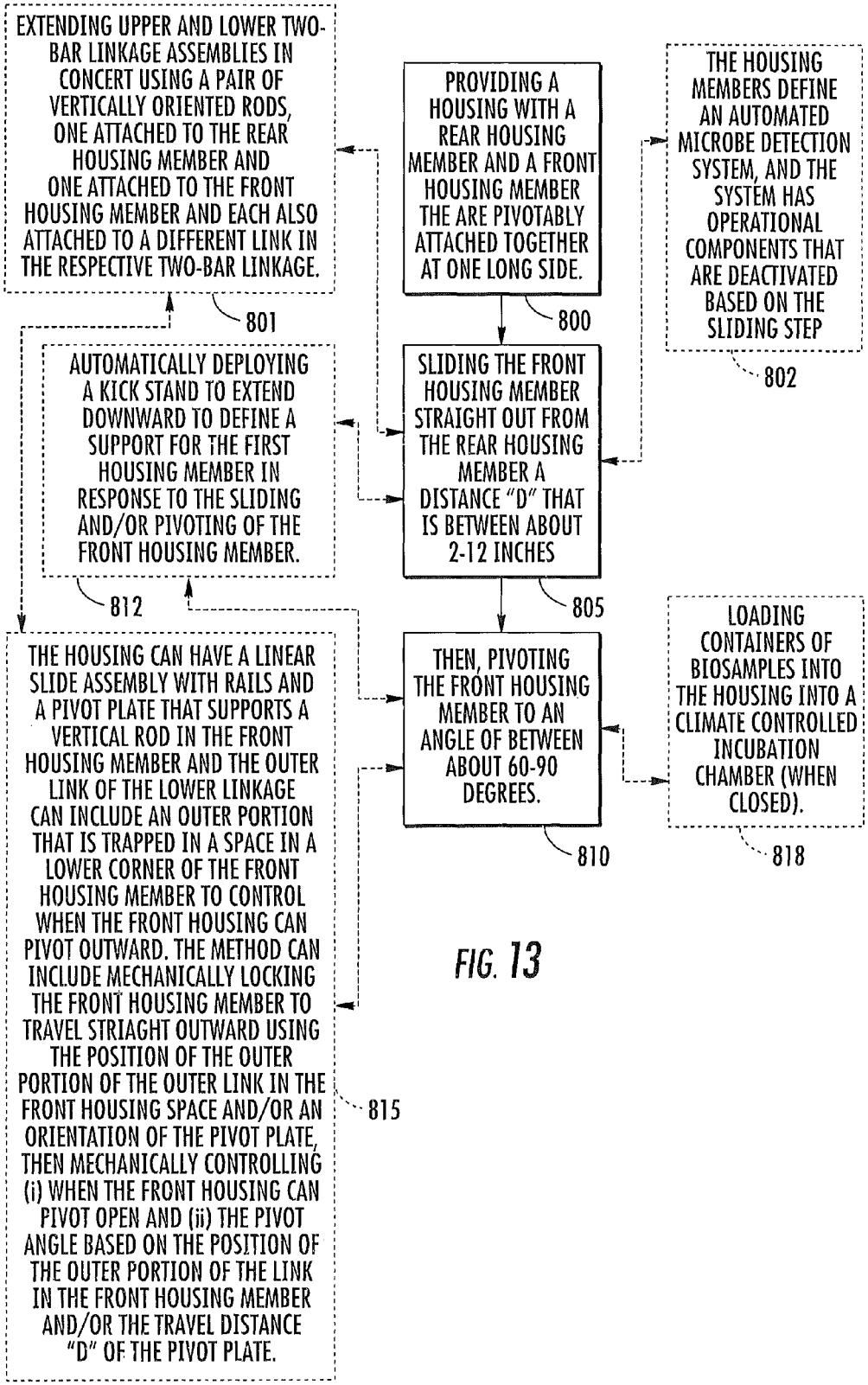
FIG. 13 is a flow chart of exemplary operations that can be used to carry out embodiments of the present invention.

FIG. 13 illustrates exemplary operations that can be used to carry out embodiments of the invention. A housing is provided with a rear housing member and a front housing member that are pivotably attached together at one long side (block 800). The front housing member is slid straight out from the rear housing member a distance "D" that is between about 2-12 inches (block 805). Then, the front housing member is pivoted open to an angle of between about 60-120 (typically about 60-100 or 80-90) degrees (block 810).

Upper and lower two-bar linkages can be extended in concert using a pair of vertically oriented rods, one attached to the rear housing member and one attached to the front housing member and each also attached to a different link in the two-bar linkage (block 801).

A kick stand can be automatically deployed to extend downwardly to define a support for the first housing member in response to the sliding or pivoting of the front housing member (block 812).

The housing can have a linear slide assembly with rails and a pivot plate that supports a vertical rod in the front housing member. The outer link of the lower linkage can include an outer portion that is trapped in a space in a lower corner of the front housing member to control when the front housing can pivot outwardly. The method can include mechanically locking the front housing member to travel straight outwardly using the position of the outer portion of the outer link in the front housing space and/or an orientation of the pivot plate, then mechanically controlling when the front housing can pivot open and the pivot angle based on the position of the outer portion of the link in the front housing member and/or the travel distance "D" of the pivot plate (block 815).

The housing members define an automated microbe detection system, and the system can have operational components that are deactivated based on the sliding step (block 802).

The method can include loading containers of biospecimens (which can optionally comprise blood samples) into the housing (when closed) into climate controlled incubation chamber (block 818).

The controller 100 (FIG. 10) can include one or more commercially available or custom microprocessor, microcontroller, digital signal processor or the like with any memory devices and/or storage media containing the software and data used to implement operations of the automated detection systems including the functionality circuits or modules used in accordance with embodiments of the present invention. The memory can include, but is not limited to, the following types of devices: ROM, PROM, EPROM, EEPROM, flash memory, SRAM, DRAM and magnetic disk. In some embodiments of the present invention, the memory may be a content addressable memory (CAM).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A housing, comprising:
    a front housing member;
    a rear housing member;
    an upper hinge assembly with first and second linkages, the first and second linkages each having opposing first and second end portions, wherein the first linkage second end portion is pivotably attached to the second end portion of the second linkage, the first linkage first end portion is attached to the front housing member, and the second linkage first end portion is attached to the rear housing member;

a lower hinge assembly with first and second linkages and a linear slide assembly, the first and second linkages each having opposing first and second end portions, wherein the first linkage second end portion is pivotably attached to the second end portion of the second linkage, the first linkage first end portion is attached to the front housing member, and the second linkage first end portion is attached to the rear housing member, wherein the linear slide assembly resides in a lower portion of the rear housing member under the first and second linkages of the lower hinge assembly and slidably engages the front housing member to define a straight linear movement of the front housing member out from the rear housing member; and first and second vertical rods that extend between the upper and lower hinge assemblies, the first vertical rod residing in the front housing member with an upper end portion of the first vertical rod attached to the first end portion of the first linkage of the upper hinge assembly and a lower end portion is attached to the linear slide assembly, and the second vertical rod residing in the rear housing member with an upper end portion of the second vertical rod attached to the first end portion of the second linkage of the upper hinge assembly, wherein the lower end portion of the second vertical rod is attached to the first end portion of the second linkage of the lower hinge assembly, and wherein the first and second linkages of the upper and lower hinge mechanisms extend outwardly in concert as the front housing member travels straight outwardly to open the housing.

2. The housing of claim 1, wherein the straight linear movement is for a defined distance "D" that is between about 2-12 inches.

3. The housing of claim 1, wherein the first end portion of the first linkage of the lower hinge assembly has an outer portion that is slidably attached to the front housing member so as to be able to travel in a space in the front housing member to control a pivot angle of the front housing member, wherein the front housing member can pivot open to an angle of between about 60-120 degrees only after the front housing member is in an extended position associated with the straight linear movement.

4. The housing of claim 1, wherein the first and second linkages of at least one of the upper and lower hinge assemblies comprise cable carrier attachment members for holding cable carriers that route power and/or data cables between components in the front and rear housing members.

5. The housing of claim 1, wherein the upper hinge assembly is adjustably attached to the front housing member and/or the rear housing member so as to be able to provide for longitudinal adjustment for alignment.

6. The housing of claim 1, wherein the linear slide assembly comprises upper and lower cooperating plates that define at least one slide rail therebetween, the upper plate configured to slide in and out while attached to the lower plate, with the lower plate affixed to a base of the rear housing member.

7. The housing of claim 1, wherein the linear slide assembly comprises first and second horizontally-oriented rigid, planar substrates with first and second parallel rails that cooperate with a corresponding slot to define linear slide tracks for the linear slide assembly.

8. The housing of claim 1, wherein the front housing member has a weight of at least about 50 pounds, wherein the housing encloses a climate controlled chamber, wherein the rear housing member has an interior volume that is larger than that of the front housing member, wherein the rear housing member has a plurality of wheels that reside on a floor, and wherein the rear housing member has a raised front base portion that resides under the lower hinge assembly.

9. The housing of claim 1, wherein the front housing member has a stowable kick stand that can be deployed into position when the front housing member is opened.

10. The housing of claim 1, wherein the front housing member has a kick stand assembly with a rear wheel that contacts a surface of a base in the rear housing member when the housing is in a closed or partially open configuration the kick stand extends vertically down when the rear wheel is forward of the base surface.

11. An automated detection apparatus for detection of microorganism growth in test samples, comprising:

a housing enclosing an interior temperature controlled chamber, the housing having a front housing member and a rear housing member;

a detection device located within the housing configured to detect microorganism growth in specimen containers loaded into the housing;

an upper hinge assembly with first and second linkages, the first and second linkages each having opposing first and second end portions, wherein the first linkage second end portion is pivotably attached to the second end portion of the second linkage, the first linkage first end portion is attached to the front housing member, and the second linkage first end portion is attached to the rear housing member;

a lower hinge assembly with first and second linkages, the first and second linkages each having opposing first and second end portions, wherein the first linkage second end portion is pivotably attached to the second end portion of the second linkage, the first linkage first end portion is attached to the front housing member, and the second linkage first end portion is attached to the rear housing member;

a linear slide assembly attached to the front and rear housing members and residing under the first or second linkages of the lower hinge assembly that slidably engages the front housing member to define a straight linear movement of the front housing member out from the rear housing member; and first and second vertical rods that extend between the upper and lower hinge assemblies, the first vertical rod residing in the front housing member with an upper end portion of the first vertical rod attached to the first end portion of the first linkage of the upper hinge assembly and a lower end portion is attached to the linear slide assembly, and the second vertical rod residing in the rear housing member with an upper end portion of the second vertical rod attached to the first end portion of the second linkage of the upper hinge assembly, wherein the lower end portion of the second vertical rod is attached to the first end portion of the second linkage of the lower hinge assembly, and wherein the first and second linkages of the upper and lower hinge mechanisms extend outwardly in concert as the front housing member travels straight outwardly to open the housing.

12. The apparatus of claim 11, wherein the linear movement is a distance "D" that is between about 2-12 inches.

13. The apparatus of claim 11, wherein the first end portion of the lower hinge assembly first linkage has an outer portion that is slidably attached to the front housing member so as to be able to travel in a space in the front housing member to control a pivot angle of the front housing member, wherein the front housing member can pivot open to an angle of between about 60-120 degrees only after the front housing member is in an extended position associated with the straight linear movement.

14. The apparatus of claim 11, wherein the first and second linkages of at least one of the upper and lower hinge assemblies comprise cable carrier attachment members for holding cable carriers that route power and/or data cables between components in the front and rear housing members.

15. The apparatus of claim 11, wherein the upper hinge assembly is adjustably attached to the front housing member and/or the rear housing member so as to be able to provide for longitudinal adjustment for alignment.

16. The apparatus of claim 11, wherein the linear slide assembly comprises upper and lower cooperating plates that define at least one slide rail therebetween, the upper plate configured to slide in and out while attached to the lower plate, with the lower plate affixed to a base of the rear housing member.

17. The apparatus of claim 11, wherein the front housing member has a kick stand assembly with a rear wheel that contacts a surface of a base in the rear housing member when the housing is in a closed or partially open configuration, and wherein the kick stand automatically extends vertically down when the rear wheel is forward of the base surface, when the front housing member is spaced apart a distance from the rear housing member.

18. The apparatus of claim 11, further comprising a second housing adjacent the first housing, and wherein the distance "D" is about 8 inches, and the angle is about 80 degrees.

19. A method of opening the housing of claim 1 to allow access to an interior thereof, comprising:
   providing the housing of claim 1;
   sliding the front housing member straight out from the rear housing member a distance "D" that is between about 2-12 inches; then
   pivoting the front housing member open to an angle of between about 60-120 degrees.

20. The method of claim 19, wherein the linear slide assembly comprises first and second horizontally-oriented rigid, planar substrates with first and second parallel rails that cooperate with a corresponding slot to define linear slide tracks for the linear slide assembly, and wherein the sliding step is carried out so that a lower two-bar linkage of the lower hinge assembly is forced to slide along the rails and upper and lower two-bar linkages are extended in concert to move one long end of the front housing member forward the distance D before allowing the pivoting.

21. The method of claim 19, further comprising automatically deploying a kick stand to extend downward to define a support for the first housing member in response to the sliding or pivoting of the front housing member.

22. The method of claim 20, wherein the linear slide assembly includes a pivot plate that supports the vertical rod in the front housing member, the method further comprising mechanically locking the front housing member to travel straight outwardly using the position of the outer member in the front housing space and/or an orientation of the pivot plate, then mechanically controlling (i) when the front housing can pivot outwardly and (ii) the pivotable angle of the front housing member based on position of an outer portion of an outer link in the front housing member and/or the travel distance "D" of the pivot plate.

* * * * *